United States Patent
Vasylyev et al.

(10) Patent No.: US 7,465,558 B2
(45) Date of Patent: Dec. 16, 2008

(54) PERFUSION SYSTEM AND APPARATUS FOR AUTOMATED MULTI-CHANNEL PATCH-CLAMP RECORDINGS UTILIZING INSIDE-OUT WHOLE-CELL CONFIGURATION

(75) Inventors: Dmytro Vasylyovych Vasylyev, Hightstown, NJ (US); Thomas L. Merrill, E. Windsor, NJ (US); Mark Robert Bowlby, Richboro, PA (US); Anton Federkiewicz, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 138 days.

(21) Appl. No.: 10/843,322

(22) Filed: May 12, 2004

(65) Prior Publication Data
US 2005/0255446 A1    Nov. 17, 2005

(51) Int. Cl.
*C12Q 1/02* (2006.01)
(52) U.S. Cl. .................................................... 435/29
(58) Field of Classification Search ........................ None
See application file for complete search history.

(56) References Cited

U.S. PATENT DOCUMENTS

| | | | |
|---|---|---|---|
| 6,048,722 A | 4/2000 | Farb et al. | |
| 6,063,260 A * | 5/2000 | Olesen et al. | 205/793 |
| 6,117,291 A | 9/2000 | Olesen et al. | |
| 6,470,226 B1 | 10/2002 | Olesen et al. | |
| 2002/0053915 A1 | 5/2002 | Weaver et al. | |
| 2003/0139336 A1 | 7/2003 | Norwood et al. | |
| 2006/0223164 A1 * | 10/2006 | Orwar et al. | 435/286.4 |

OTHER PUBLICATIONS

E. Neher et al., The extracellular patch clamp: a method for resolving currents through individual open channels in biological membranes, Pflugers Arch 375, 219-228 (1978).

* cited by examiner

*Primary Examiner*—Christopher R. Tate
*Assistant Examiner*—Amanda P Wood
(74) *Attorney, Agent, or Firm*—Hunton & Williams LLP

(57) ABSTRACT

A system and method for high throughput patch clamp measurements to study the effect of various chemicals on ion transfer channels is provided. One or more patch clamp configurations is established, each comprising a cell sealed to a pipette. The pipettes are affixed to a pipette fixture. The pipette fixture and a plate comprising one or more wells are relatively moved so that each cell is inside a well. Electrical properties of the cells are measured.

24 Claims, 21 Drawing Sheets

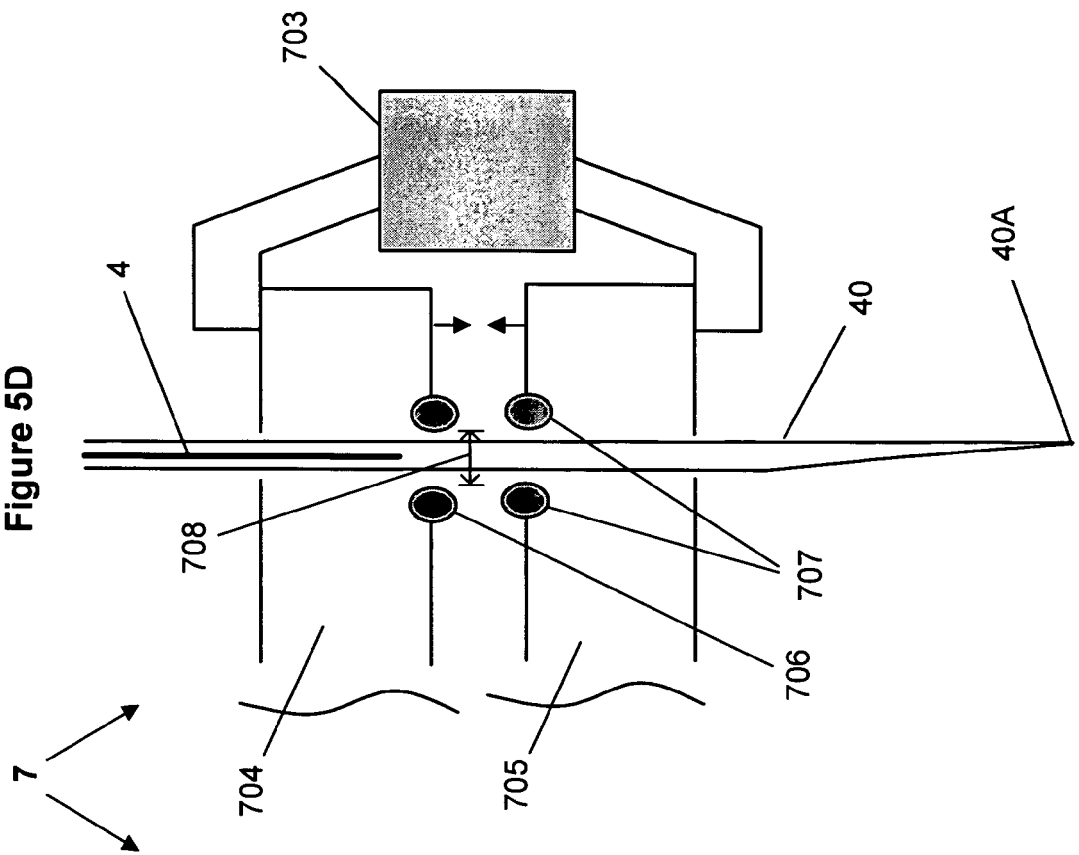
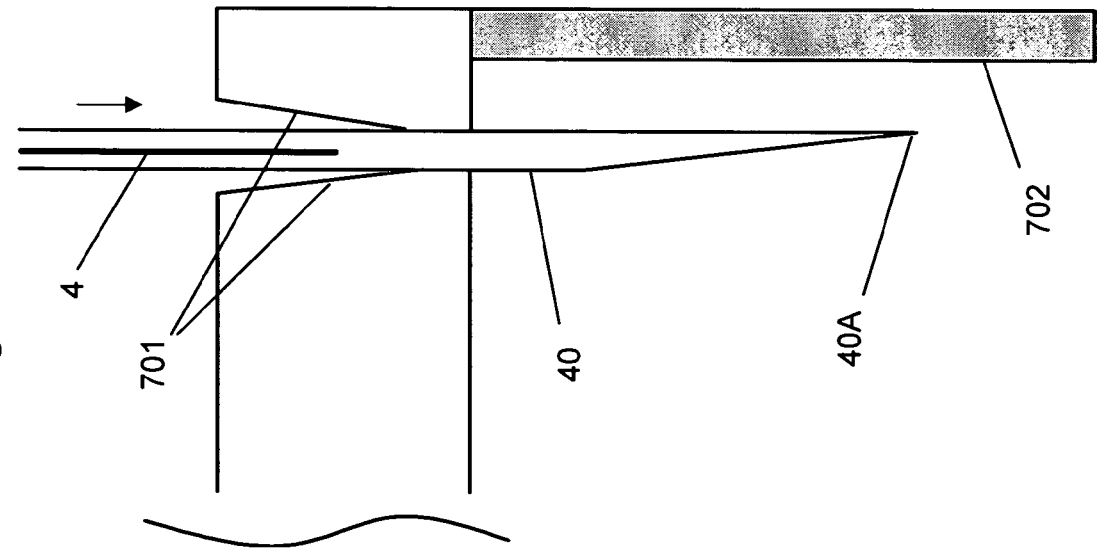

US 7,465,558 B2

PERFUSION SYSTEM AND APPARATUS FOR AUTOMATED MULTI-CHANNEL PATCH-CLAMP RECORDINGS UTILIZING INSIDE-OUT WHOLE-CELL CONFIGURATION

FIELD OF THE INVENTION

The invention relates to a multi-channel system for carrying out patch clamp techniques to study biological membranes. More particularly, this invention relates to patch clamp systems having high throughput and low volume requirements. The invention more broadly refers to testing the electrophysiological effects of drugs and other chemicals. The invention also provides an apparatus for high throughput chemical screening and methods of using the same.

BACKGROUND OF THE INVENTION

Many cellular processes are controlled by changes in cell membrane potential due to the action of carrier proteins and ion channels. Carrier proteins bind specific solutes and transfer them across the lipid bilayer of biological cell membranes by undergoing conformational changes that expose the solute binding site sequentially on one side of the membrane and then on the other.

Unlike carrier proteins, ion channel proteins are transmembrane proteins that form pores in biological membranes which allow ions and other molecules to pass from one side to the other. There are various types of ion channels, for instance, "leak channels," "voltage-gated channels," "ligand-gated channels," and channels modulated by interactions with proteins, such as G-proteins.

Ion channel proteins primarily mediate the permeation of a particular ion. For example, sodium ($Na^+$), potassium ($K^+$), chloride ($Cl^-$), and calcium ($Ca^{2+}$) channels have been identified. Ion channels are largely responsible for creating the cell membrane potential, which is the difference in the electrical charge on the opposite sides of the cell membrane (B. Alberts et al., supra).

The wide variety of carrier proteins and ion channels represents a rich collection of new targets for pharmaceutical agents. Many chemicals, compounds, and ligands are known to affect carrier protein and/or ion channel activity.

Ion channel activity can be measured using the technique of patch-clamp analysis. The general idea of electrically isolating a patch of membrane using a micropipette and studying the channel proteins in that patch under voltage-clamp conditions was outlined by Neher, Sakmann, and Steinback in "The Extracellular Patch Clamp, A Method For Resolving Currents Through Individual Open Channels In Biological Membranes," *Pflueger Arch.* 375; 219-278, 1978.

The patch clamp technique represents a major development in biology and medicine. For example, the technique allows measurement of ion flow through single ion channel proteins, and allows the study of single ion channel responses to drugs. Briefly, in a standard patch clamp technique, a thin glass pipette (with a tip typically about 1 µm in diameter) is pressed against the surface of a cell membrane. The pipette tip seals tightly to the cell and isolates a few ion channel proteins in a tiny patch of membrane. The activity of these channels can be measured electrically (single channel recording) or, alternatively, the patch of membrane can be ruptured allowing the channel activity of the entire cell membrane to be measured (whole cell recording).

During both single channel recording and whole-cell recording, the activity of individual channel subtypes can be further resolved by imposing a "voltage clamp" across the membrane. Through the use of a feedback loop, the "voltage clamp" imposes a voltage gradient across the membrane, limiting and controlling overall channel activity and allowing resolution of discrete channel subtypes.

The time resolution and voltage control in such experiments are impressive, often in the msec or even µsec-range. However, a major obstacle of the patch clamp technique as a general method in pharmacological screening has been the limited number of compounds that could be tested per day. In addition, the standard techniques are further limited by the slow rate of sample compound change, and the spatial precision required by the patch-clamp pipettes.

A major factor limiting throughput of the patch clamp technique is the perfusion system, which directs the dissolved test compound to cells and patches. In other words, the cells are perfused (i.e., bathed) in a solution, and the test compound is directed into the solution so that its effect on the cell can be measured. In traditional patch clamp setups, cells are placed in large experimental chambers (0.2-2 ml wells), which are continuously perfused with a physiological salt solution. Chemicals are then applied by switching the chamber inlet to a valve connected to a small number of solution bottles containing the chemical(s). However, this technique has several drawbacks. First, the number of different compounds which may be connected at one time is limited by the number of feeding bottles. Second, the volumes required for test samples and supporting fluid require large amounts of costly chemicals. Third, the time required to change the solute composition around cells and patches remains high, and this is a rate-limiting step. Accordingly, there have been several attempts to increase the throughput capacity of patch-clamp recordings.

The development of sophisticated systems for local application of compounds to activate neurotransmitter-regulated channels, like the U-capillary and other systems, has reduced effective application times. However, the volume of bath solution exchanged by such fast application systems is quite large. Such large volume requirements limit the use of these procedures in the medical industry due to the high costs of reagent and the extensive time required to test tens of thousands of chemicals in varying concentrations. These prior art systems are further limited by the inflexibility and low capacity of the feeding systems that fill the U-capillary, which are virtually identical to the systems used in conventional patch clamp experiments.

U.S. application Ser. No. 09/900,627 filed Jul. 6, 2001 by Weaver et. al. ("Weaver") discloses a system that can measure electrical properties of cells. The Weaver system does not use a pipette tip to attach to cell membranes. Rather, a plurality of pores on a porous surface attach and seal to a plurality of cell membranes. One side of the porous surface is coupled to a ground electrode, and the other side is coupled to a measuring electrode. In one embodiment where the porous surface is a microchip, each cell may be attached to its own ground and measuring electrodes, allowing for cell-specific measurements. When test solutions are applied to one or more sides of the porous surface, a patch clamp recording can be measured for the attached cells. The system can be automated so that multiple porous surfaces are tested simultaneously on a multi-well plate.

U.S. patent application Ser. No. 10/239,046 (Pub. No. U.S. 2003/0139336 A1) filed Mar. 21, 2001 by Norwood et. al. ("Norwood") provides an automated system for establishing a patch clamp configuration. Norwood's system is limited to attaching a patch pipette to a cell located at the liquid-air interface of a suspended liquid, such as a drop of liquid suspended from the bottom of a capillary tube. Increasing (or decreasing) pressure inside the tube causes the meniscus, the liquid-air interface, to bulge outward (or inward). In the Norwood system, the cell is outside the patch pipette before it is patched. Also, the air pressure system is applied to a second tube that holds and suspends the cellular liquid; air pressure is not applied to the patch pipette itself.

U.S. Pat. Nos. 6,063,260, 6,117,291, and 6,470,226 to Olesen et. al. (collectively, "Olesen") disclose a high throughput patch clamp system wherein a computerized motor control system causes a patch pipette to patch a cell automatically selected from a cell bath. The pipette tip and cell then remain affixed in a perfusion chamber for patch clamp measurements. An autosampler controls a valve that alternately directs fluid from various sources into the perfusion chamber, including one or more test chemical solutions and washing solutions. Thus, in the Olesen system a number of tubes and pumps are used to pump test chemicals and washing baths into and out of the perfusion chamber.

U.S. Pat. No. 6,048,722 to Farb et. al. ("Farb") discloses an automatic patch clamp perfusion system that perfuses patched cells with a plurality of test and wash solutions. The test and wash solutions drain from a plurality of reservoirs through a multi-barrel manifold into a recording chamber, which contains a patched cell. A valve controls which solution perfuses the cell at a given time. As in the Olesen system, the Farb system involves a number of tubes and pumps to pump test chemicals and washing baths into and out of the recording chamber.

The disclosures of Weaver, Norwood, Olesen, and Farb are incorporated herein by reference in their entirety.

There remains a need for faster, cheaper methods of high throughput screening. Such high-throughput screens would be invaluable for the search and identification of agents that modulate ion channel activity. In turn, such agents would be useful for the treatment of various diseases.

SUMMARY OF THE INVENTION

According to an embodiment of the invention, a system and method for high throughput patch clamp measurements to study the effect of various chemicals on ion transfer channels is provided. One or more patch clamp configurations is established, each comprising a cell sealed to a pipette. The pipettes are affixed to a pipette fixture. The pipette fixture and a plate comprising one or more wells are relatively moved so that each cell is inside a well. Electrical properties of the cells are measured.

According to another embodiment of the invention, a computer-readable medium encoded with computer program code to automate a patch clamp measurement system is provided. The program code effective to perform the following steps. One or more cells are loaded into one or more tips of one or more pipettes. The one or more pipettes are affixed to a pipette fixture. The pipette fixture and a plate comprising one or more wells are relatively moved so that the each of the one or more cells is inside each of one or more first wells, respectively. At least one electrical property of each of the one or more cells is measured.

According to another embodiment of the invention, an apparatus for measuring properties of a membrane is provided. A pipette fixture is coupled to one or more pipettes, wherein each pipette is adapted to provide a high electrical resistance seal with a membrane in a patch clamp configuration at the tip of each pipette. A motorized platform comprises one or more multi-well plates. A motor controller is configured to relatively move the motorized platform and the pipette fixture so that each tip of the one or more pipettes is inside the one or more wells.

The invention provides a system for multi-channel patch clamping and utilizes the system for screening of chemical substances such as drug compounds. In particular, the system may be used to accelerate the study of the effect of chemical compounds on ion channel transfer.

One embodiment of the invention provides for the testing of the intracellular regions of ion channels for an entire cell. Another embodiment of the invention provides a whole-cell configuration stable enough to enable conducting multiple tests on single cells. Another embodiment of the invention provides for a whole-cell configuration that has a high diffusion characteristic which enables the cell to be washed of drug compounds rapidly, accelerating the ion channel screening process.

One embodiment of the invention may be employed to make single cell measurements and recordings. Another embodiment of the invention may be employed for automated patch clamp recordings wherein multiple single cells are attached to multiple electrodes. Automating a patch clamp according to this embodiment reduces errors associated with manual manipulations and waveform analysis. Automating a plurality of patch clamps according to this embodiment increases the speed and throughput of the patch clamp experiments. In particular, automation enables the precise timing of agent application (e.g., the addition of chemicals, compounds, or ligands) and improves the quality of experimental data by reducing inadvertent errors, idiosyncratic variations in protocol between different investigators, and noise caused by manual manipulations. Because the efficiency and speed of testing is increased, automation allows mass, parallel screenings of large chemical libraries. This is especially advantageous for screening agents that affect ion channel activity and thus cellular electrical properties (e.g., cell membrane conditions).

Another embodiment of the invention leverages existing technology and simplifies existing procedures to reduce the cost of automated patch clamping.

In another embodiment of the invention, an apparatus for conducting high throughput patch clamp measurements is provided. The apparatus comprises conventional electronics for conducting patch clamp measurements, comprising: a headstage, a main amplifier, and an electrode; a multi-channel pipette fixture for holding one or more pipettes during patch clamp measurements; a pipette holder for holding one or more pipettes in a vertical orientation; a platform for holding the pipette holder and one or more multi-well compound plates, the compound plates comprising a test compound; an air pressure control system capable of moving a cell to the tip of a pipette; an XYZ lead screw robot for controlling the motion of the platform in the x-, y-, and z-directions, the compound plate(s), and the pipette holder(s); and a data acquisition and control system for acquiring data, controlling robot movement, and adjusting air pressures. This apparatus is particularly advantageous since automated handling equipment and robotics are commercially available. For instance, one such automated robotics system is the BiSlide XYZ available from Velmex, Inc.

Another embodiment of the invention provides a fluid wash system for removing test compounds from cells, comprising one or more cylindrical or cone-shaped troughs capable of being perfused with a liquid, and a pump connected to the trough(s), said pump capable of perfusing the trough(s) with a liquid. The fluid wash system may optionally comprise internal vanes for use in directing the fluid motion of the liquid.

In another embodiment of the invention, a method is provided for conducting patch clamp measurements. The method comprises: creating an inside-out whole cell patch clamp configuration by positioning at least one cell inside the tip of at least one pipette and then exposing the cell to ambient air; positioning a compound plate comprising a series of test compounds so that it engages a first row of pipettes; conducting a patch-clamp measurement of the cell(s) as it is in contact with the test compound; disengaging the compound plate from the pipette fixture; conducting a rinsing step; positioning the compound plate so that it engages a second row of pipettes; conducting a patch-clamp measurement of the cell (s) as it is in contact with the test compounds; and repeating the rinsing and measuring steps as many times as desired, wherein the same compound plate or a different compound plate is engaged to a row of pipettes during each repetition.

Another embodiment of the invention is directed to a method of conducting high throughput patch clamp measurements, comprising loading a cell into a pipette, wherein said pipette comprises an electrode; placing the pipette in a pipette holder, said pipette holder located on a moveable platform, wherein said platform is capable of holding one or more compound plates and/or a fluid wash system; moving the platform relative to a pipette fixture, wherein the pipette fixture is connected to an air pressure control system, and wherein the pipette is positioned so as to attach to the pipette fixture; moving the platform relative to the pipette fixture, wherein the pipette is disengaged from the pipette holder, and wherein the pipette is stably attached to the pipette fixture; moving the platform relative to the pipette fixture, wherein the tip of the pipette is contacted with the compound plate, said compound plate comprising a plurality of wells comprising a first set of test compounds; using the air pressure control system to position the cell at the tip of the pipette, wherein the cell is in contact with both the electrode and the first test compound; and measuring the electrical activity of the cell contacted with the first test compound.

In an alternative embodiment of the method of conducting high throughput patch clamp measurements, after electrical activity of the cell contacted with the first test compound is measured, the plate and fixture are relatively moved again so that the pipettes are removed from the first set of wells and then inserted into a second set of wells on the same plate. The cells are again removed and re-inserted into a new set of wells, and the removal and insertion process can repeat for any number of times. A wash system and the fixture may be relatively moved so that the cells are inserted into the wash system, and the wash system can wash the cells by passing washing liquid over the cells. The cells may be washed before or after each cell measurement, or at other times.

The foregoing and other objects, advantages, and characterizing features of the invention will become apparent from the following description of certain illustrative embodiments thereof considered together with the accompanying drawings, wherein like reference numerals signify like elements throughout the various figures.

DESCRIPTION OF THE DRAWINGS

FIGS. 5A-5D illustrates an exemplary pipette holder subassembly.

DETAILED DESCRIPTION OF THE INVENTION

Figure 1:
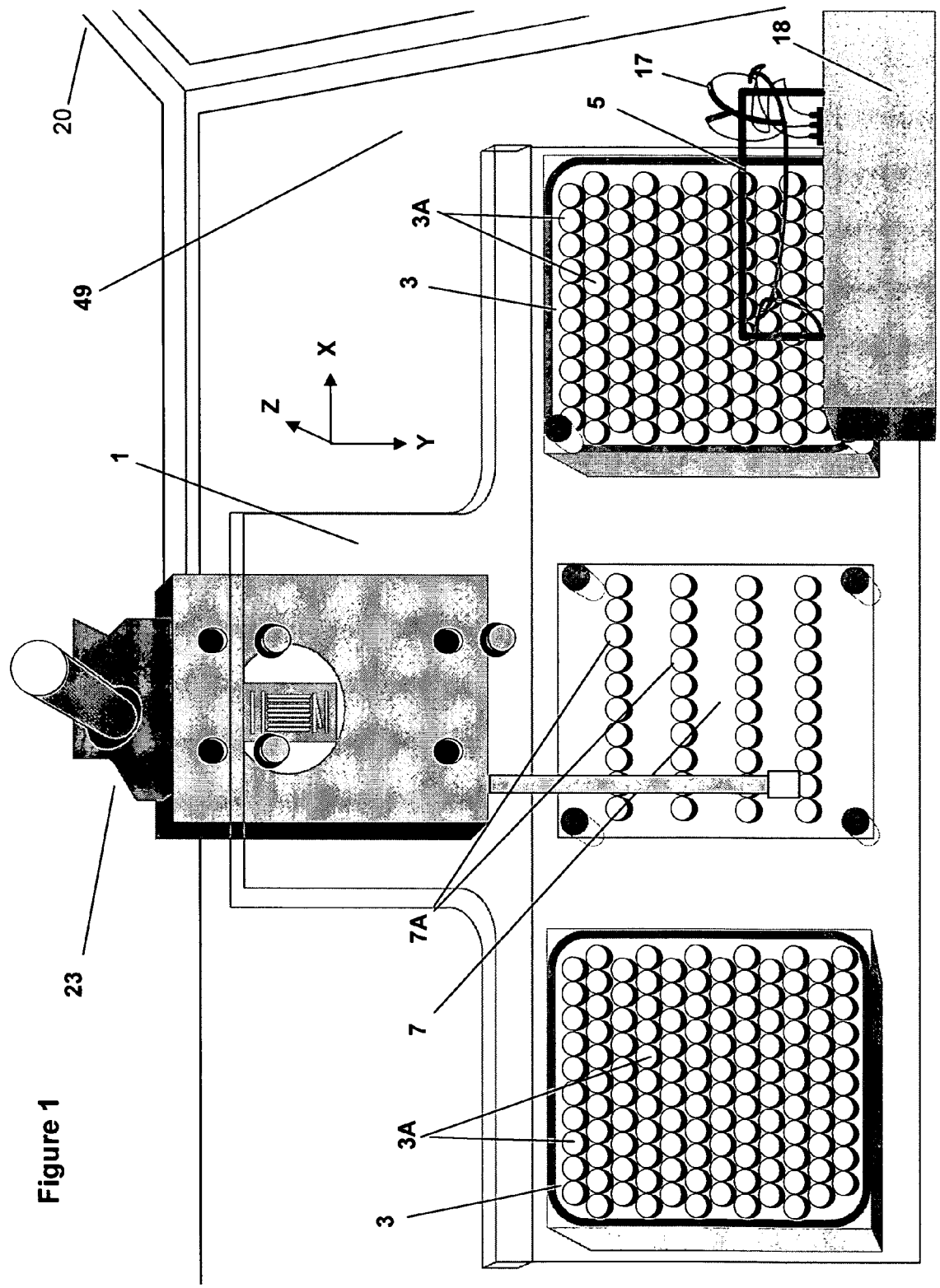
FIG. 1 shows a top view of an exemplary multi-channel patch clamp system.

The subject matter of this invention is related to the U.S. Application entitled "Fast Perfusion System and Patch Clamp Technique Utilizing An Interface Chamber System Having High Throughput And Low Volume Requirements," filed May 3, 2004 under Attorney Docket No. 38523.000061. This application is incorporated herein by reference in its entirety.

A preferred embodiment of the invention is shown in FIGS. 1-10. A platform 1 may be used to hold one or more multi-well compound plates 3, pipette holder 7, and optionally a fluid wash system 21. Pipettes 40 are preloaded with cells 30 to be tested. The pipette holder 7 may be used to store the pipettes 40 with preloaded cells 30. A disposal area 49 may optionally be used to collect used and discarded pipettes 40. A pipette fixture 5 comprising fixture connectors 17 is configured to secure and suspend the pipettes 40 during patch clamping. A stand 6 may be used to hold the head stage electronics 18 and the fixture connectors 17. An air pressure control system 70 may be used to push and pull cells 30 and/or to manipulate the pipettes 40. To wash the tips of the pipettes 40 between each well 3A row, a separate fluid system 21 may be used to remove compounds. A robot 23 may be used to control the motion of the platform 1, the 96-well plates 3, and/or the pipette fixture 5. A data acquisition and control system 25 may be used to acquire data, control robot 23 movement, and adjust air pressures.

FIG. 1 shows the top-down view of a multi-channel patch clamp system according to an embodiment of the invention. The system comprises an XYZ robot 23, a motor driven platform 1, a pipette holder 7 for storing pipettes, well plates 3 comprising one or more reservoirs 3A, a disposal area 49 for used pipettes, a pipette fixture 5 comprising fixture connectors 17, and head stage electronics 18. A Faraday cage 20 surrounds and encloses the patch clamp system.

Figure 6:
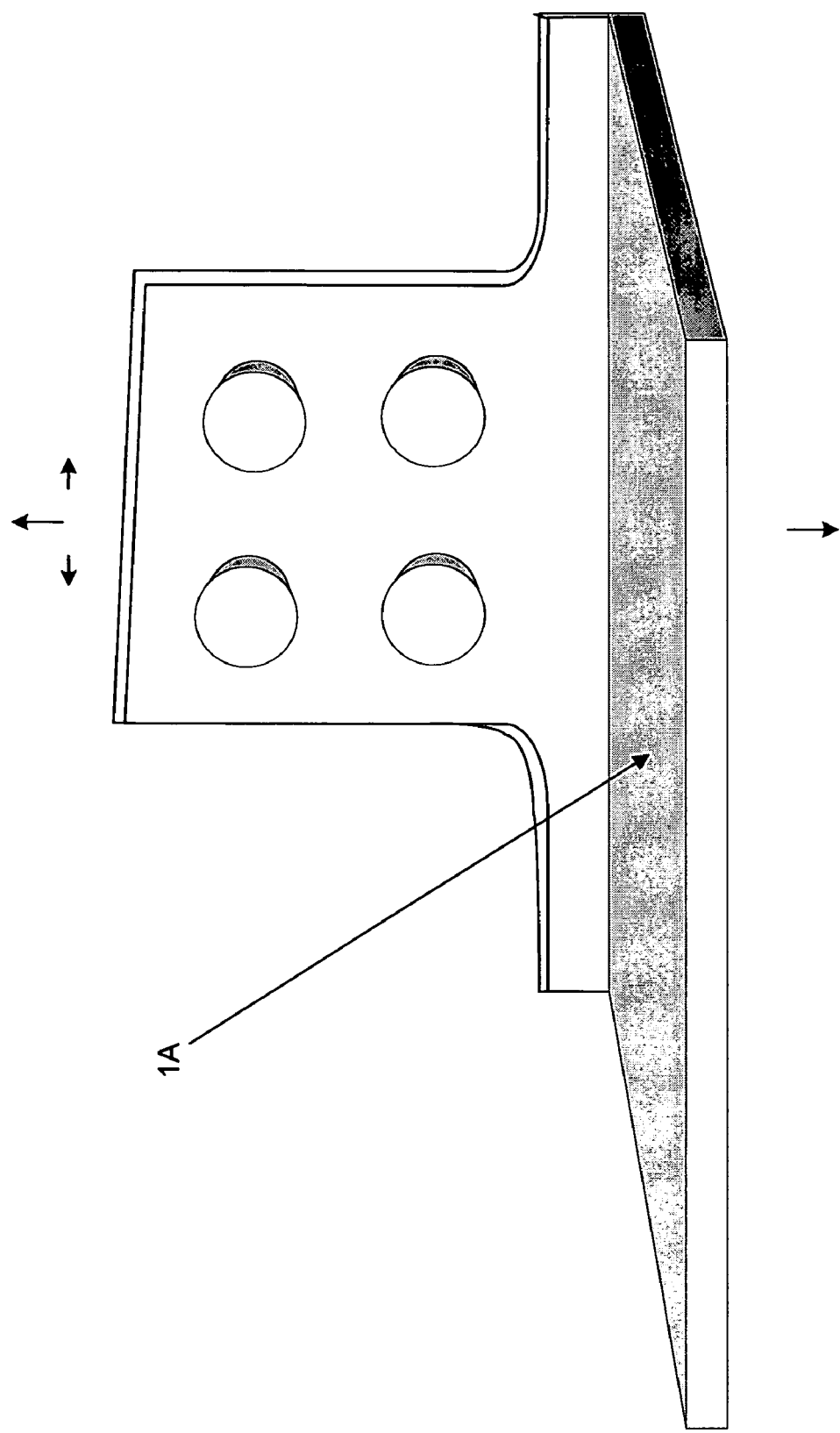
FIG. 6 illustrates an exemplary plate.

The moveable platform 1 is preferably large enough to accommodate one or more multi-well compound plates 3, one or more pipette holder(s) 7, and a fluid wash system 21. (An isometric drawing of the platform 1 is shown in FIG. 6.) The platform 1 is preferably motor driven, and more preferably is driven by a 3-axis lead screw robot 23 that utilizes stepper motors (see FIG. 3). As shown in FIG. 1 the platform 1 may be bolted to a carriage that is mounted on a lead screw. A 3-axis lead screw robot 23 is commercially available, and may be purchased from Velmex, Inc.

The moveable platform 1 is coupled to the well plate(s) 3 and the pre-loaded pipette holder(s) 7. For instance, the well plates 3 and pipette holders 7 may be platforms resting on and/or affixed to the moveable platform 1. The platform 1 is movable in the x-, y-, and z-directions. Thus, the platform 1 can be moved up, down, left, right, diagonally in any direction, or in any non-linear 3-dimensional path. The platform 1 is configured to move the well plates 3 and pipette holder 7. For instance, it may move the pipette holder 7 and well plates 3 (at different times) into a position directly beneath the pipette fixture 5.

Each of the one or more multi-well plates 3 preferably comprises one or more wells 3A. As used herein, the term "well" refers to any surface capable of containing a small volume of liquid. This includes reservoirs and depressions, as well as flat surfaces wherein a small volume of liquid forms a distinct droplet of liquid, held together by the surface tension of the liquid. The well plate 3 may have a high concentration of shallow wells 3A, such as 48- to 384-well plates, wherein the shallow wells 3A are arranged in rows and/or columns on the well plate 3 such as in an 8×12 matrix configuration. For instance, the plate 3 may comprise a 48-(6×8) or a 96-(8×12) well format compound plate. Such an arrangement is useful for automating the filling of the wells 3A and contacting the tips of the pipettes 40 with the liquid in wells 3A. The high density of wells 3A per compound plate preferably reduces the amount of test chemical or compound that is required during testing and speeds the movement between wells.

The wells 3A are configured to contain one or more test substances, neutral solutions, or wash solutions. The test substance may comprise a drug or other chemical. Preferably, the test substance comprises a chemical that has an effect on the ion channels of a membrane. The neutral solution may comprise any inert liquid, such as an inert aqueous or saline solution. Preferably, the neutral solution does not chemically react or interfere with the cell and cell membrane. The wash solution may comprise any solution that can wash a cell, e.g., by washing away a test substance.

Each well 3A can preferably hold a minimum liquid volume (such as a volume of test solution) of about 10 uL and a maximum liquid volume of about 10 mL. These volumes correspond to the volume of test solution required to conduct an accurate patch clamp measurement. The minimum volumes that may be accommodated by the wells 3A may be 10 uL, 20 uL, 30 uL, 50 uL, and 80 uL. The maximum volumes that may be accommodated may be 0.5 mL, 1 mL, 2 mL, and 5 mL. The test solution volume may be any combination of these minimum and maximum values; for instance, the volume may be between 30 uL and 0.5 mL, or between 50 uL and 5 mL. More preferably, the volume is between 20 uL and 1 mL. For instance, there may be a 96-well plate wherein each well is designed to hold up to 0.3-0.35 mL of solution. The wells 3A may also comprise a neutral solution such as a saline solution. For instance, some of the wells 3A (or rows of wells) may comprise a test substance in one or more different concentrations, while other wells (or rows of wells) on the same or different plate may contain a neutral solution or a wash solution.

The pipette holder 7 may comprise any means for holding and/or storing one or more pipettes. The pipette holder 7 may comprise a plurality of holding mechanisms 7A, such as circular openings of a size and shape such that a pipette can be inserted into the opening 7A and be held in place by the wall of the opening 7A. For instance, a pipette may have a pipette tip that is more narrow than the opening 7A, and a central portion of the pipette may be more wide than the opening 7A. When a pipette is inserted into the pipette holder 7, the pipette tip may fit through the hole, but the wider portion of the pipette may couple to the opening 7A and cause the pipette to be held in place by the opening 7A. The pipette holder 7 may thereby hold one or more pipettes prior to (or after) patch clamp measurements.

The pipette holder 7 is affixed to the movable platform 1. Pipettes held by the pipette holder 7 may be moved by moving the platform 1. For instance, the pre-loaded pipettes may be moved via the movable platform 1 so that they are affixed to the pipette fixture 5 (see FIG. 4B).

The pipette fixture 5 is also configured to hold pipettes, although it is preferably not coupled to the moveable platform 1. Pipettes held by the pipette holder 7 may be transferred to the pipette fixture 5 by moving the platform 1 (and consequently the pipette holder 7) so that pipettes held by the pipette holder 7 are directly beneath the pipette fixture 1. The pipette holder 7 may then be moved upward toward the fixture 5 so that the pipettes attach to the fixture 5. For instance, the pipettes may be inserted into the fixture, wherein the fixture is configured to affix to the pipettes. The pipette holder 7 may then be lowered, and the pipette holder 7 will no longer be coupled to the pipettes. In one embodiment, the pipette holder 7 releases its grip on the pipettes after the pipettes are coupled to the pipette fixture 5.

By using the moveable platform 1 to move the well plates 3 upward toward the pipette fixture 5, the cell in the pipette tip can be effectively inserted into the test substance (or wash fluid) in a well 3A. At this point, patch clamp measurements can be taken using electrodes and the head stage electronics 18 as explained below.

In accordance with the present invention, the disclosed apparatuses utilize conventional electronics for patch clamp measurements, including a headstage, HEKA EPC9/2 patch-clamp amplifier, and/or any other commercially available or locally-made amplifier(s) and one or more electrodes. Preferably, the apparatuses of the invention utilize amplifiers that are designed to process multichannel data and facilitate simultaneous recordings. Current, voltage, resistance, capacitance, and other electrical recordings may be acquired for each amplifier. Data filtering and analog to digital processing can be applied, and the data may be stored on a computer, e.g., the data acquisition and control system 25.

The head stage electronics 18 are configured to control the electronics of patch clamp measurements. Such electronics are well-known in the art. For instance, the head stage electronics 18 may comprise a HEKA EPC9 2-channel amplifier. The head stage electronics 18 are used in conjunction with a main amplifier and one or more electrodes. For instance, the electronics 18 may measure the voltage and/or current across one or more electrodes connected to the electronics 18, as in a patch clamp measurement. In such a patch clamp measurement, a separate electrode (preferably wire) serves as a reference electrode, and the other electrode serves as the measuring electrode. The connectors 17 connect the head stage electronics 18 to the electrodes, to the data acquisition and control system 25 and from the reference electrode to the headstage.

The data acquisition and control system 25 may comprise a processor, a database, and/or a computer. The data acquisition and control system 25 is coupled, preferably via wires, to the head stage electronics 18. The data acquisition and control system 25 may also be coupled (e.g., via wires and other electronic control mechanisms) to the air pressure control system 70, robot 23, and platform 1.

The data acquisition and control system 25 controls robot 23 movement, patch clamp electronics and signal capture, and air pressure control. For example, a program such as visual basic 6.0 interface (or another program) may be utilized to coordinate Velmex's XYZ-3D stage software 25, HEKA's Pulse software, and signals to and from the air pressure control system 70. The software controls the operation of the components 1, 70, 23, and any other electronic components in the system. For instance, the software may control the measuring functions of electrodes for taking patch clamp measurements. Computer software for controlling and monitoring automated cell electrophysiology apparatuses has been described in detail and is well known in the art (see, for example, U.S. Pat. No. 6,048,722 to Farb et. al.).

Preferably, the software or automation routine integrates test chemical or compound delivery, instrument control, data acquisition, and waveform analysis through an on-screen interface. For instance, a user may interface with and/or control the operation of the patch clamp system of FIG. 1 using traditional computer inputs such as a mouse, keyboard, joystick, or other input device. In this way, all aspects of the patch clamp recording session can be controlled through the on-screen interface by using the mouse (or other input device) to adjust instrument controls. For example, automated protocols can be developed to initiate and carry out dose-response, reversal potential, modulator effect and repetitive application experiments with a single key press. In addition, waveform analysis routines can automatically measure parameters such as response amplitude, onset time, and desensitization time constant, and then save this information directly to a disk, such as a disk coupled to the data acquisition and control system 25.

Figure 2:
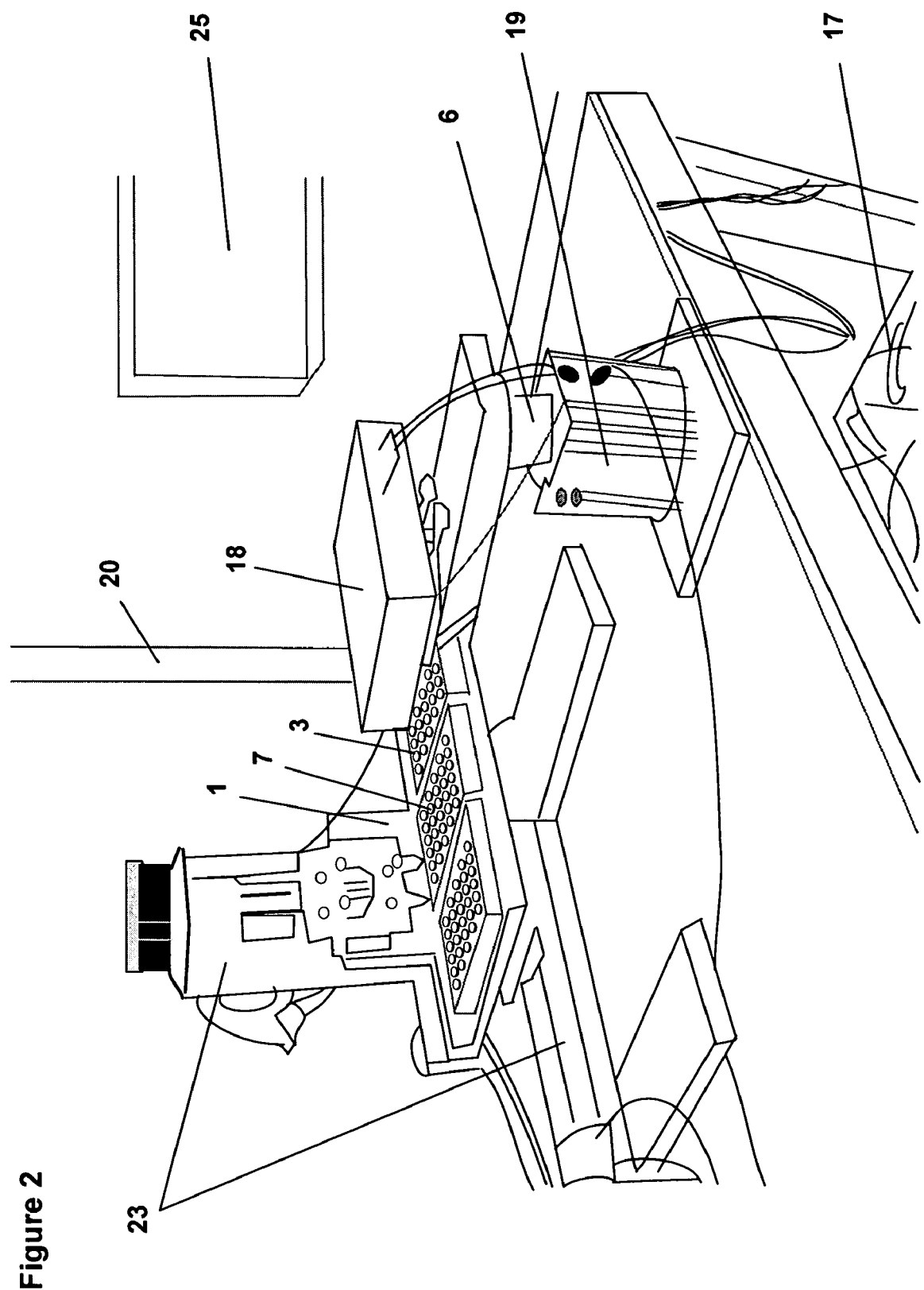
FIG. 2 shows a front view of the multi-channel pipette system of FIG. 1.

The Faraday cage 20 surrounds the patch clamp system (see FIG. 2). The Faraday cage 20 eliminates unwanted electric fields inside the cage, such as those that would otherwise be caused by sources outside the cage. This is advantageous because patch clamp measurements require highly sensitive electronic measurements which would be impaired by unwanted electric fields. Thus, the Faraday cage 20 encloses the patch clamp measuring components (such as the pipettes, cells, and electrodes) and separates them from the data acquisition and control system 25 and other electrical components and wiring that may cause unwanted electrical interference with patch clamp measurements.

The disposal area 49 is an area where used pipettes can be stored after patch clamp measurements are made. For instance, by applying a pulse of high pressure to the pipettes 40 while they are affixed to the pipette fixture 5, the pipettes may be ejected from the fixture 5 into the disposal area 49. The pipettes may also simply be dropped into the disposal area 49, for instance, if the pipette fixture 5 loosens its attachment to the pipettes or otherwise disengages the pipettes. Other methods of transferring one or more pipettes or other objects from one place to another may be considered.

FIG. 2 shows the front right view of the multi-channel pipette system of FIG. 1. FIG. 2 shows the support stand 6, air pressure control system 70, the data acquisition and control system 25, the XYZ robot 23, the moveable platform 1, the one or more well plates 3, the pipette holder 7, and the Faraday cage 20.

The support stand 6 may support the head stage electronics 18 and/or pipette fixture 5 (not shown). The support stand 6 may comprise any support stand as well-known in the art. Preferably the support stand 6 is stationary. However, in one embodiment, the support stand is a moveable device that can move the pipette fixture 5. For instance, the support stand 6 may cause the pipette fixture to move to a position above the disposal area 49 so that pipettes can be dropped from the pipette fixture 5 into the disposal area 49.

The air pressure control system 70 is configured to control air pressure inside each pipette. By applying air pressure inside the pipette, the air pressure control system 70 may cause a cell inside the pipette to move toward the tip of the pipette, as described further in FIG. 10.

Figure 3:
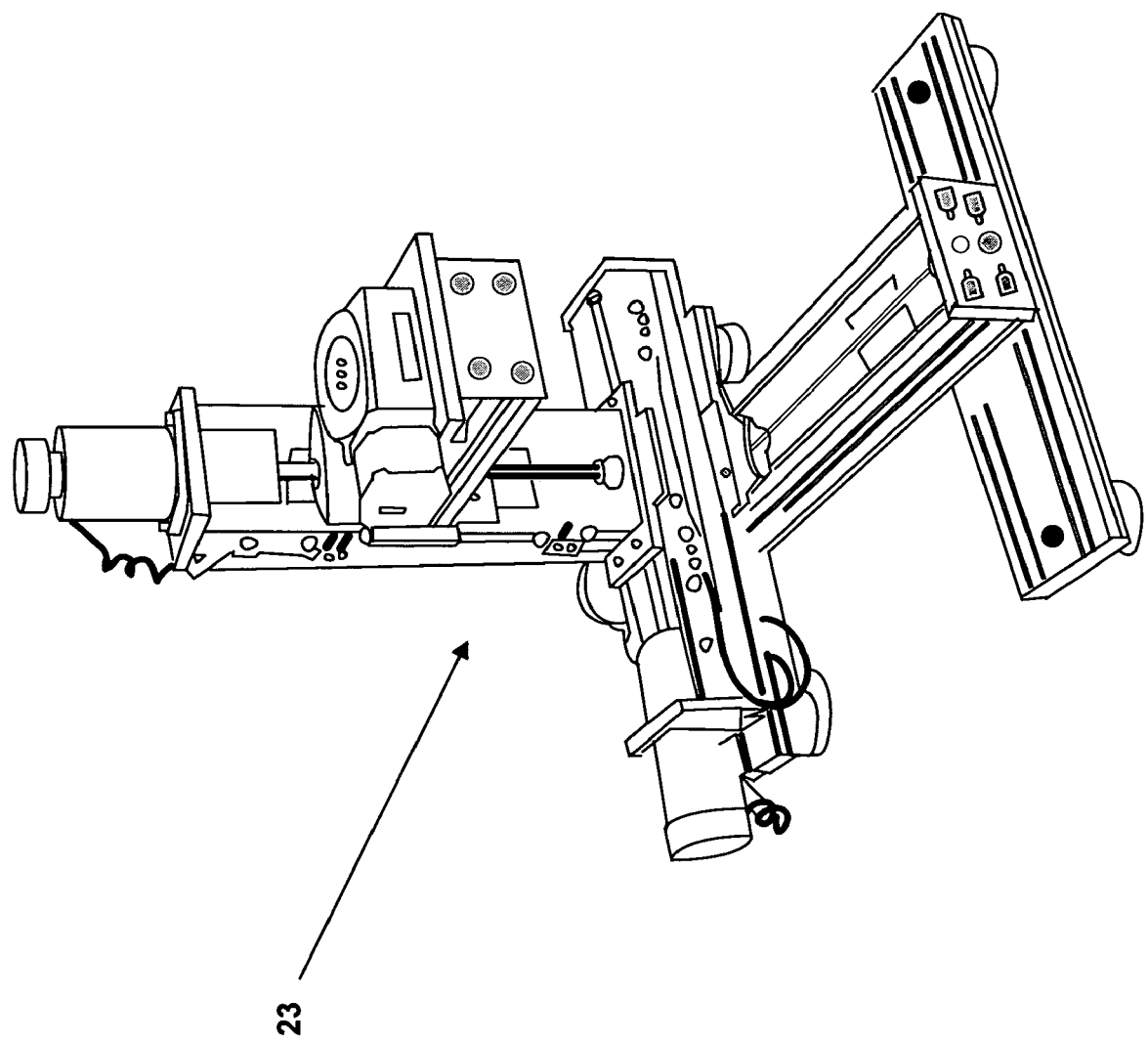
FIG. 3 shows an exemplary XYZ lead screw robot.

FIG. 3 shows an exemplary embodiment of the robot 23 in greater detail. As shown in the diagram, the robot 23 comprises a 3-axis motorized (via stepper motors) platform from Velmex controlled by a PC via RS232 communication protocol. A Plexiglas plate comprising 48 (or 96, etc.) well plates is coupled to a Velmex 3-axis platform. The robot 23 preferably controls the motion of the platform, and thus controls the motion of the well plate(s) 3, the pipette holder(s) 7, and/or the fluid wash system 21. As discussed above, the robot's 23 movements may be controlled by a data acquisition and control system 25.

Figure 4A:
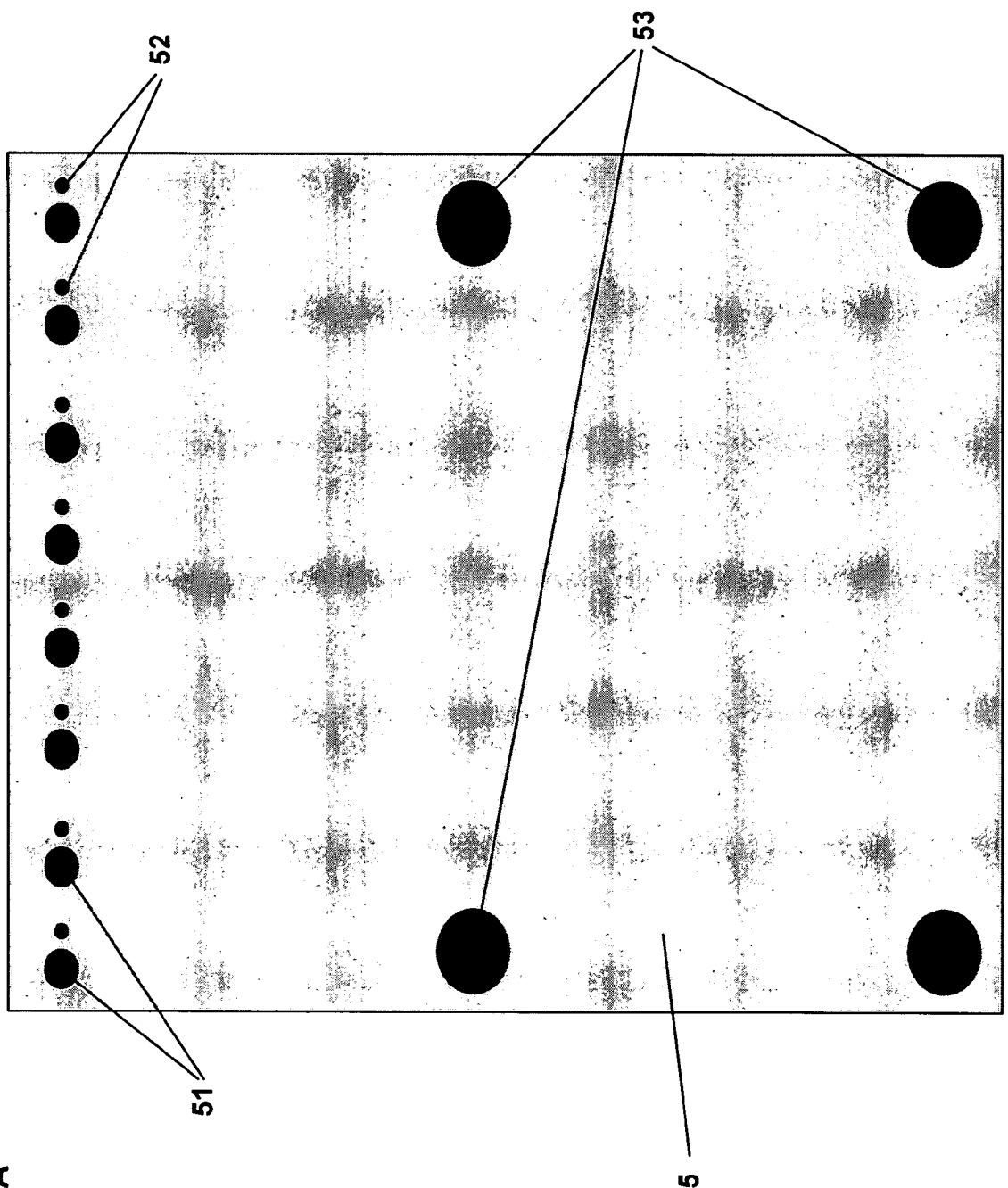
FIGS. 4A-4C illustrates an exemplary pipette fixture subassembly.
Figure 4B:
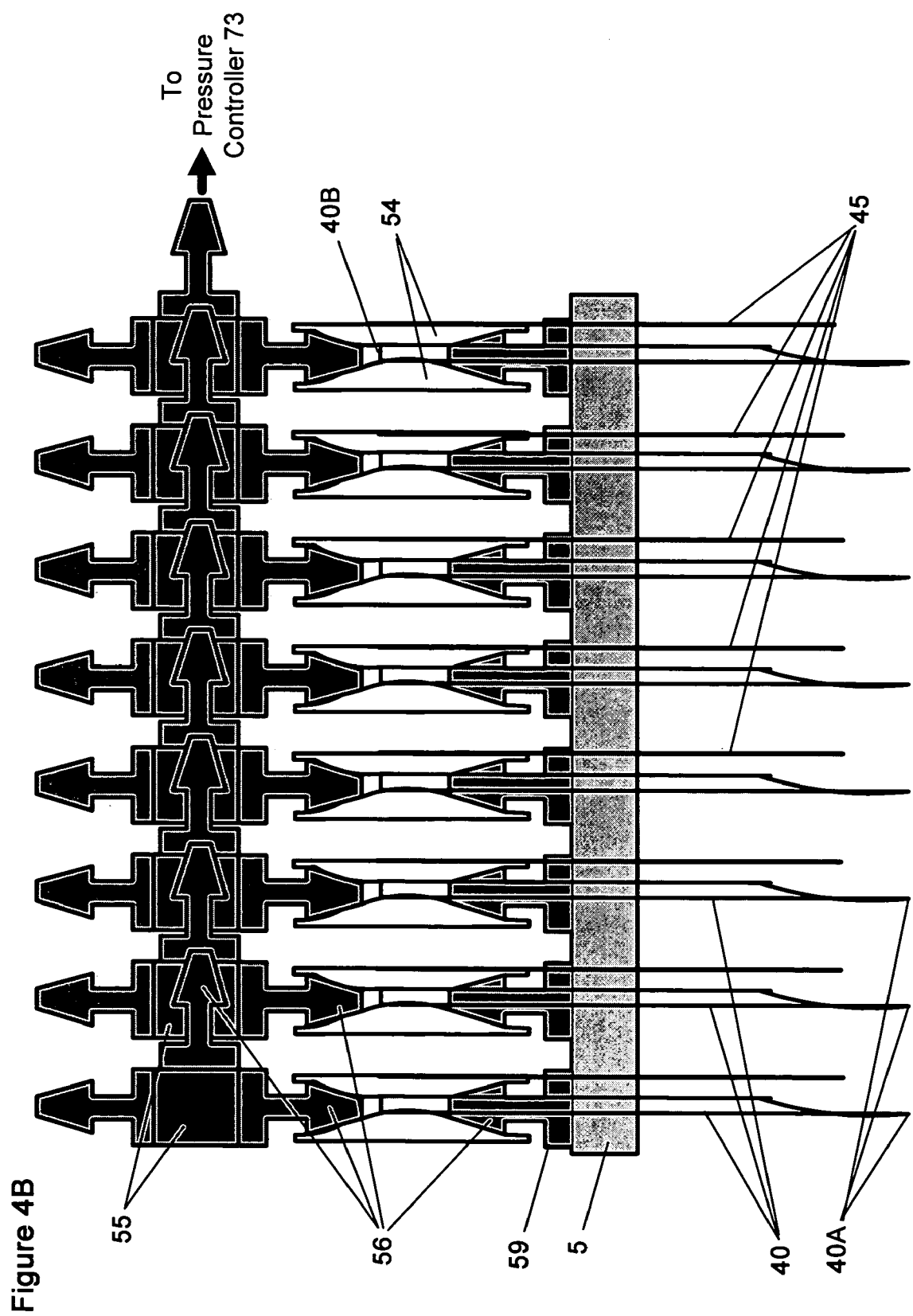
Figure 4C:
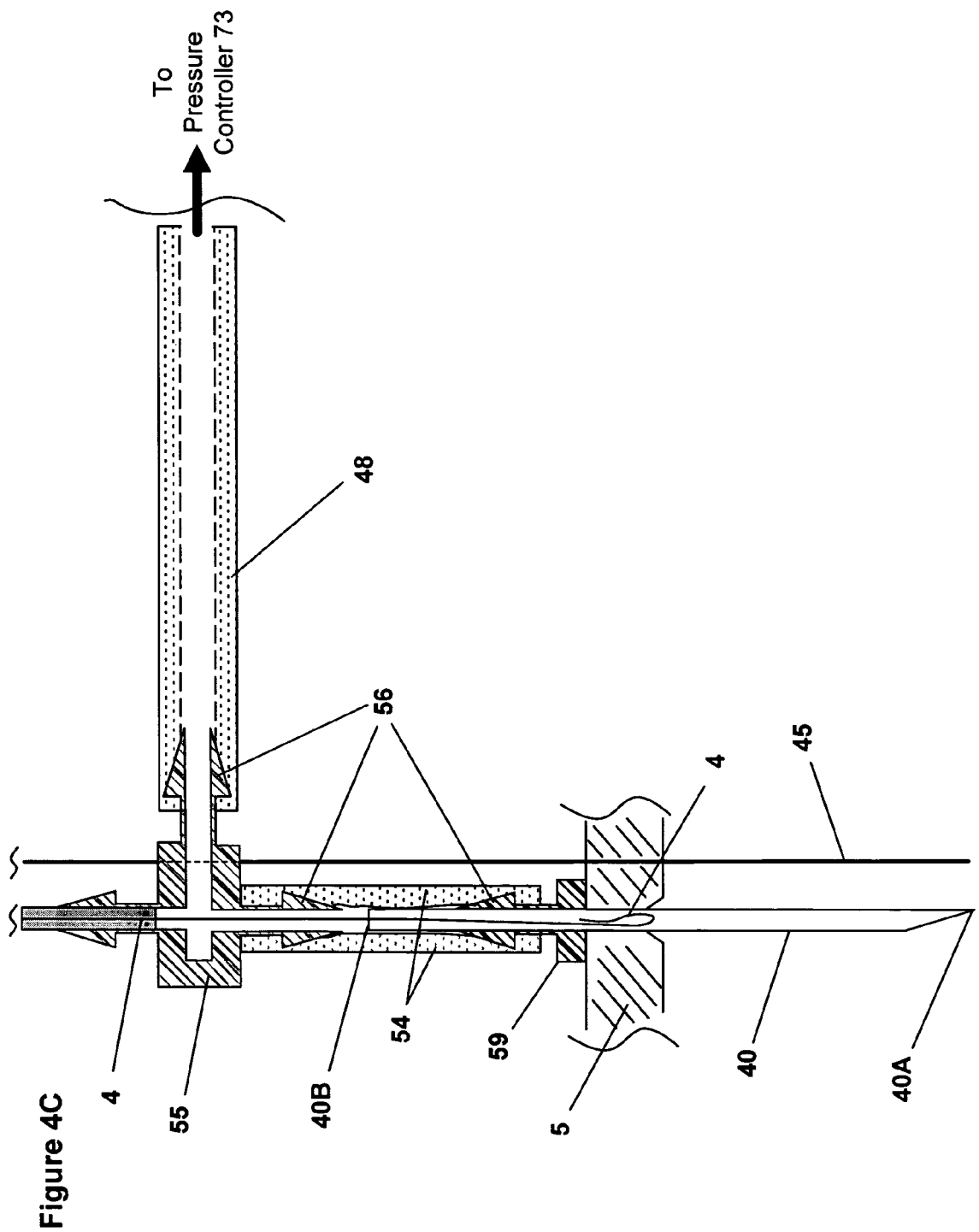

FIGS. 4A-4C show the pipette fixture 5 according to an embodiment of the invention. The pipette fixture 5 preferably comprises fixture connectors 17 which may be used to secure and suspend the pipettes 40 during patch clamping. The pipette fixture 5 may thereby be capable of attaching to the pipettes 40 (or, alternatively, the pipettes 40 may be capable of attaching to the pipette fixture 5). The pipette fixture 5 may hold the pipettes 40 in a constant and substantially vertical position. The pipette fixture 5 may also be used to connect the air pressure control system 70 and the reference electrode 45.

It should be noted that for each channel in the current system, there may be two electrodes: an electrode outside the patch pipette (bath and/or reference electrode 45) and an electrode 4 inside the patch pipette. Both electrodes 4, 45 may be coupled to the same amplifier. The amplifier may measure current and/or voltage between these two electrodes 4, 45. The measurement information may be used to measure properties of the cellular membrane. It should be further noted that the pipette may be a glass pipette, a patch pipette or a microelectrode depending on its shape and electrical resistance.

FIG. 4A shows a top view of the pipette fixture 5. The pipette fixture 5 comprises a plurality of openings 51 to accommodate one or more pipettes 40. A smaller opening 52 next to each large opening 51 may accommodate reference electrodes 45 (e.g., bath electrodes) that may be used for carrying out patch clamp measurements. Support holes 53 may be used to secure the fixture, e.g., using a screw or other coupling device.

FIG. 4B shows a cross-sectional side view of eight pipettes 40 and reference electrodes 45 held in a constant vertical orientation by the pipette fixture 5. Air pressure in the pipette is applied via side port of holder 57.

The pipettes 40 may comprise any tubular device or any portion of a device that is tubular and/or cylindrical in shape. The pipette 40 is hollow at one or both ends. For instance, the pipette 40 may be any capillary tube, such as a micropipette. The pipette comprises a pipette tip 40A. The tip 40A preferably defines an opening that is approximately circular in shape. The tip of the pipette 40 may be of a size and shape that allows it to be attached to a cell 30 or cell membrane 30A (see FIGS. 10A-10C), such as a mammalian, insect, amphibian, or other cell. For instance, the opening of the tip 10A may have a diameter of approximately 0.1 to 10 microns. Preferably, the opening of the tip 10A has a diameter of approximately 1 micrometer. When the pipette 40 is attached to a cell 30, it is sometimes called a patch pipette. As used herein, the term "patch pipette" refers to any tube used in patch clamping techniques that attaches to a cell 30.

Preferably, the pipette 40 can be made from any non-conductive material which seals tightly to biological membranes, has dielectrical properties advantageous for patch clamp measurements, and is substantially inert to a wide range of chemicals. More preferably, the pipette 40 is made from glass and/or plastic (e.g. polystyrene).

In one embodiment of the invention, a polyurethane tube placed between the barbed connector and the barbed tee may be used to hold the pipettes 40 in position and maintain an air-tight connection for the air pressure control system 70. The pipette fixture 5 may engage and secure the pipettes 40 at various points along the axis of each pipette 40 in order to hold each pipette 40 in place. The tip of each pipette 40 may extend beyond the surface of pipette fixture 5 so that the tips of the pipettes 40 are exposed for easier access to the cell 30 for patch clamp measurements and cell washings.

A substantially vertical position of a pipette 40 helps to stabilize the cell 30 at the tip of the pipette 40 for patch clamp measurements. A constant position is helpful for maintaining the gigaseal between the cell 30 and the pipette tip 40A. Also, typically the cells 30 are more dense than the fluid 41 inside the pipettes 40, and so a vertical position of the pipettes helps to keep the cells at the bottom tip 40A of the pipettes 40.

FIG. 4C shows a cross-sectional side view of a single pipette 40 (of FIG. 4B) coupled to the pipette fixture 5. As shown in FIG. 4C, each pipette may be held in place by a polyurethane (or other polymer or similar material) tube 54. For example, the pipette 40 may coupled to the pipette fixture 5 when the motorized platform 1 causes the pipette fixture 5 to couple to the pipettes 40. For instance, the pipette fixture 5 may "grab" the pipette 40 from the pipette holder 7. In "grabbing" each pipette (and/or "grabbing" a set of pipettes 40 at the same time), the pipette 40 may be inserted into the pipette fixture 5 into the position shown in FIG. 4C. As shown in FIG. 4C, the pipette may extend vertically through a hole in the pipette fixture 5, through a bottom plastic fixture 59 affixed to the pipette fixture 5, and up through tubing 54. The upper tip 40B of the pipette 40 may rest between the bottom plastic fixture 59 and an upper plastic fixture 55. The pipette 40 may accordingly be held in place by the pipette fixture 5, plastic fixture 59, and tubing 54. The upper tip 40B may be open so that air can enter and leave the pipette through the tip 40B.

It should be appreciated that the tubing 54 and some of the other elements shown in FIG. 4C may be cylindrical or otherwise circular in shape, even though this cross-sectional side view does not show the circular shape. For example, tubing 54 may comprise a single piece of cylindrical tubing that extends above and below the page of the diagram, and it may define a cavity that may contain a portion of the pipette 40, plastic fixtures 56, and air that may flow into or out of the pipette 40.

The upper plastic fixture 55 may comprise a barbed "t" shape. A downward facing portion may comprise a barbed plastic fixture 56 that extends in the direction of the pipette 40. An upward facing portion may comprise a solid portion 55A that allows the electrode 4 to pass (e.g., to the DAS 25) but otherwise creates an airtight seal around the electrode 4 and prevents air from escaping into or out of the plastic fixture 55. A horizontal portion may comprise another barbed plastic fixture 56 coupled to (and surrounded by) flexible tubing 58. The flexible tubing 58, upper plastic fixture 55, and flexible tubing 56 may together comprise an airtight path for air (and changes in air pressure) to travel between the pressure controller 73 and the pipette 40.

The polyurethane tube 54 may connect plastic fixtures 56. Plastic fixtures 56 may comprise barbed fittings to help ensure an airtight seal between the tube 54 and plastic fixtures 56, which may help to prevent outside air from entering the pipette 40. For a given pipette 40, the tube 54 (as shown in FIGS. 4B and 4C) may extend vertically from one plastic fixture 59 coupled to pipette 40 to another plastic fixture 55 situated above the top edge of the pipette 40B. Plastic fixture 59 may be coupled to the pipette fixture 5.

The pipettes 40 may be press-fit into the polymer tubing 54 (which may be compliant) between the plastic fixtures 56. The pipette 40 may force the tubing 54 to expand and then contract along the outside wall of the pipette, e.g., when the pipette is first inserted into the position shown in FIG. 4B.

Figure 7:
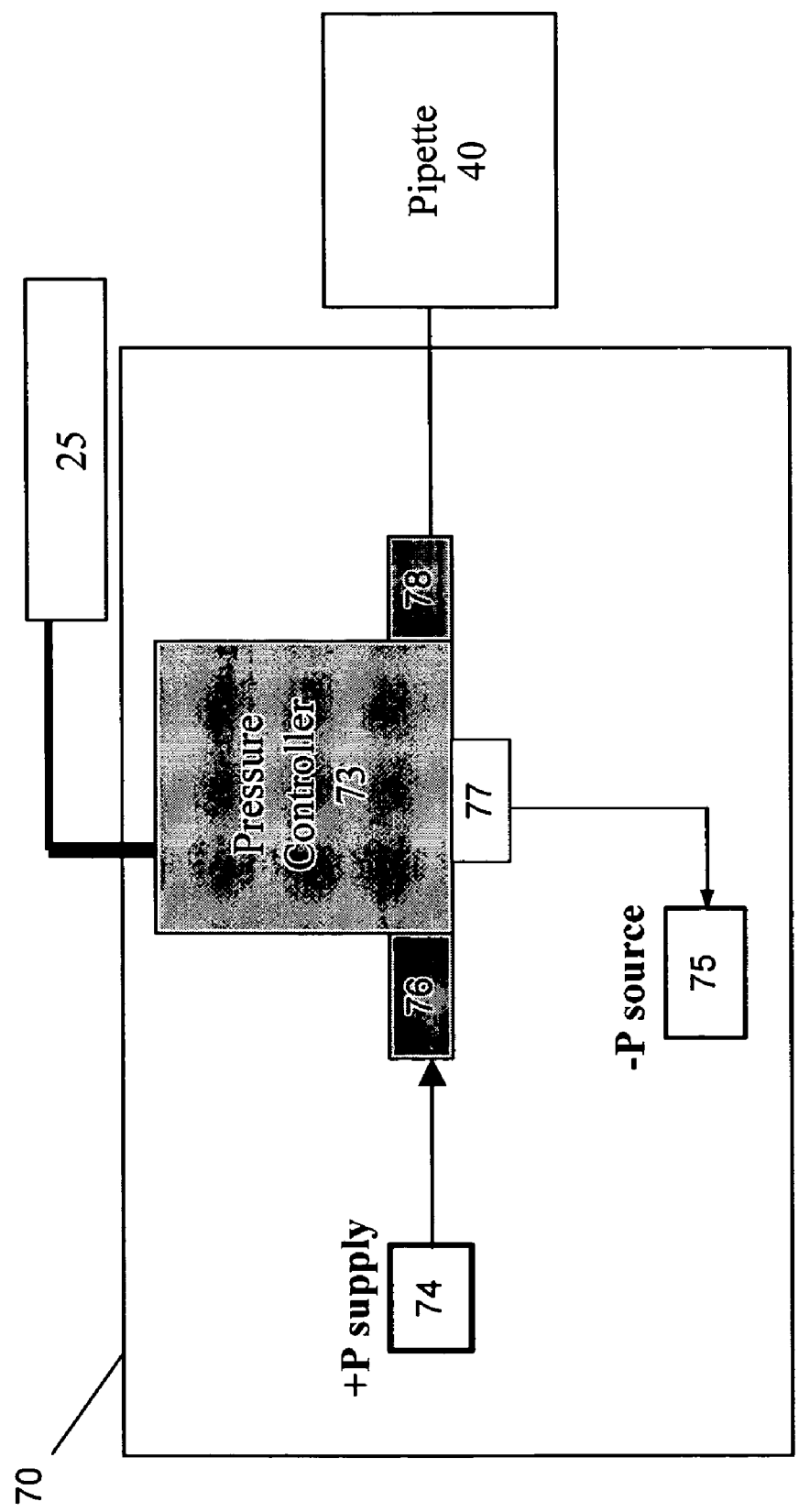
FIG. 7 illustrates an exemplary air pressure control system.

Another set of tubing 58 (or possibly the same tubing 54) may connect to the pressure controller 73 (see FIG. 7). The tubing 54, 58 and plastic fixtures may comprise a continuous, airtight connection between the pressure controller 73 (not shown) and the inside of the pipette 40. In other words, the tubing may provide an unobstructed, continuous path of air between the pressure controller 73 and the pipette 40. Each pipette 40 may have a separate tubing system 58 that connects to the pressure controller 73. In this way, the gigaseal for each pipette can be separately created and monitored. In other embodiments, the pipettes 40 may share a connection.

Each pipette 40 preferably comprises an electrode 4 (see also FIGS. 10A-C). The electrode 4 may be inside the pipette 40, and it may be attached to an electronic amplifier. As used herein, the term "electrode" refers to a physical transmitter or conductor of electric signals from the pipette solution to an amplifier. When the electrode 4 is inside the pipette 40 and touching the capillary solution 41, the pipette 40 is a patch electrode. As used herein, the term "patch electrode" refers to a patch pipette further comprising an electrode 4, all of which attaches to the cell (not shown). Accordingly, the terms "patch electrode" and "capillary electrode" are interchangeable for purposes of this invention.

The electrode 4 may be attached to a device (e.g., a patch clamp amplifier) that measures current and/or voltage between the electrode 4 and another reference, such as a reference or bath electrode 45. In some embodiments, one or more of the electrodes 4, 45 may comprise a microelectrode. As used herein, the term "microelectrode" refers to a patch electrode of appropriate size for recording signals from individual cells 30. Preferably the tip of the patch electrode 4 is brought into contact with a cell (or a solution 41 in contact with the cell) to enable measuring electrical properties of the cell 30 in a patch clamp configuration. As used herein, the term "patch clamp" refers to a patch electrode configuration that allows the recording of signals from a biological membrane by placing a patch electrode in contact with a small area of the cell membrane 30A. The patch clamp may be a "whole-cell patch clamp," (see FIGS. 10A-C) which refers to a patch electrode configuration that allows the recording of signals from the entire membrane of a cell 30 by placing a patch electrode 4 in contact with a small area of the cell membrane 30A and then rupturing that small area of membrane 30A (the patch). Generally, this may be done as an "inside-out whole-cell" when a cell is placed inside the pipette 40 and the patch of membrane is ruptured via air exposure.

As shown in FIGS. 4B and 4C, the end of the patch electrode 4 that is inside the pipette 40 may have a curl. In some embodiments, the curl avoids binding and interference problems when the pipette 40 is pushed upwards through the fixture 5 and into the flexible tubing 54 that creates the seal.

Figure 5A:
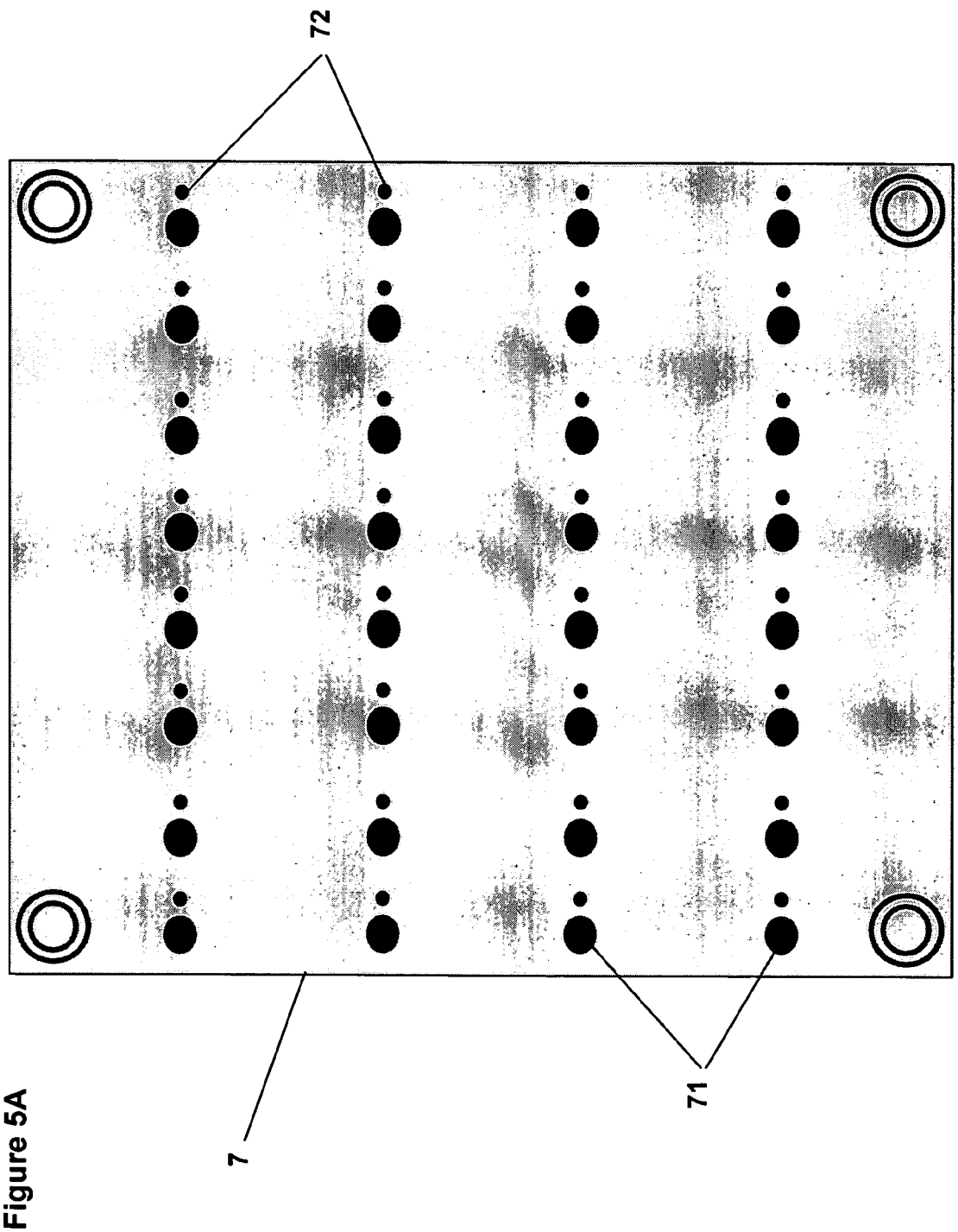
Figure 5B:
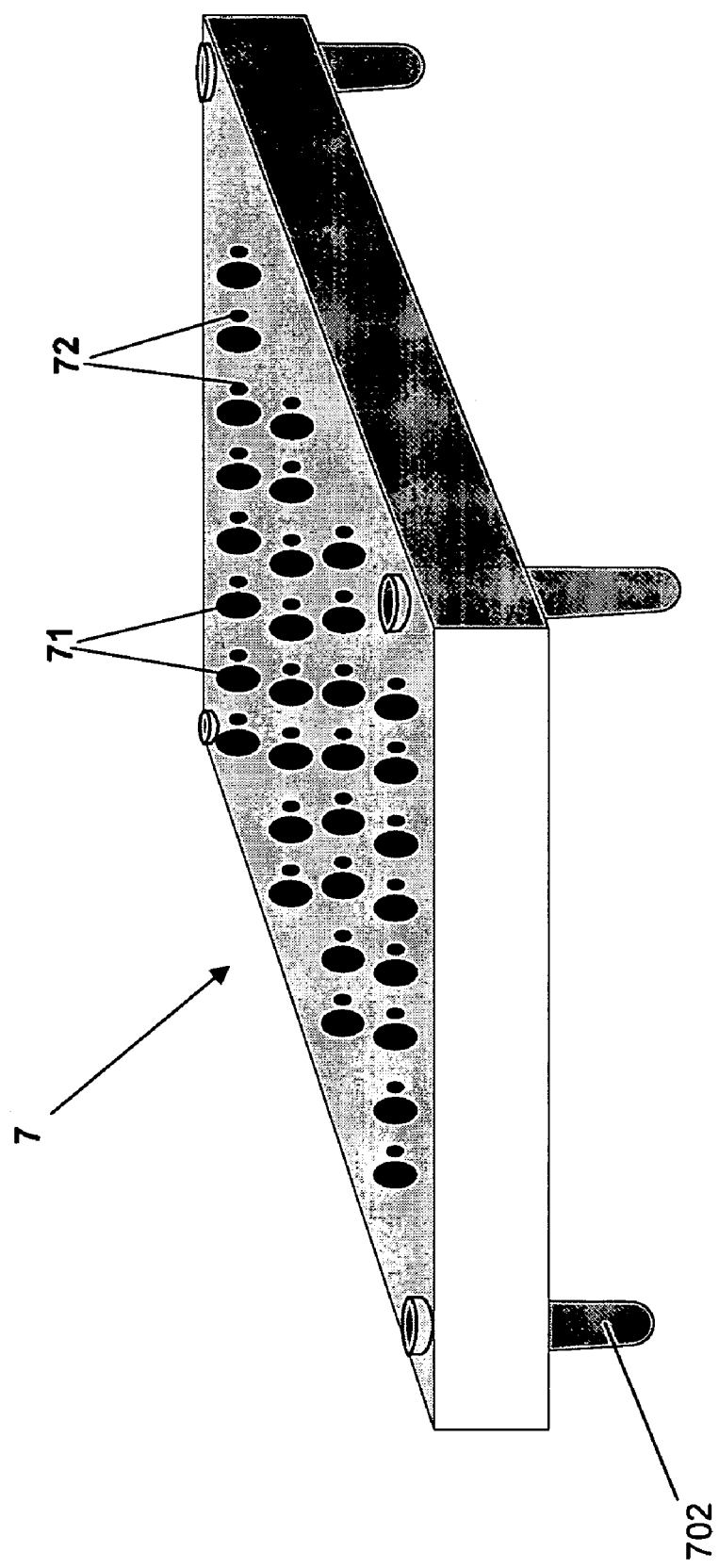

FIGS. 5A-5D show an exemplary embodiment of the pipette holder 7. FIG. 5A shows the top view of the pipette holder 7, and FIG. 5B shows a side view of the pipette holder 7.

The pipette holder 7 may include any surface with one or more holes, grooves, or coupling devices to enable pipettes 40 to be affixed thereon or stored therein. For instance, pipettes 40 may be inserted into holes in the pipette holder 7 so that the pipettes 40 rest in the pipette holder 7 in a vertical or substantially vertical position, wherein the pipette holder 7 is a generally flat surface in the horizontal plane. The tips of the pipettes 40 may stick through the bottom side of the pipette holder, and the remainder of the pipettes 40 may stick out above the surface of the pipette holder 7 (see FIGS. 5A-D).

The pipette holder 7 may comprise a plurality of openings 71 to accommodate preloaded pipettes 40 before the pipettes 40 are loaded into the pipette fixture 5. A smaller opening 72 next to each large opening 71 may accommodate reference electrodes 45. Preferably, the pipette holder 7 has multiple rows of openings 71 for holding multiple groupings of preloaded pipettes 40. For instance, one grouping of pipettes may contain cells of a given size, age, measurement history, type, temperature, bath solution, or other similar characteristic. The pipette holder 7 may also comprise a support leg 702, which may support the pipette holder 7 and keep the holder 7 a sufficient distance from the ground (or other surface) so that a pipette 40 in the holder cannot touch the ground while sitting in the pipette holder 7.

In a preferred embodiment of the invention, the pipette holder 7 holds the preloaded pipettes 40 in a substantially vertical orientation so that the pipette fixture 5 can easily engage the pipettes 40. The preloaded pipettes 40 in the pipette holder 7 may be loaded into the pipette fixture 5 when the robot 23 moves the pipettes 40 to a position underneath the pipette fixture 5 and then raises the pipette holder 7 so that the pipettes 40 are secured by the pipette fixture 5.

FIGS. 5C and 5D show two different approaches to holding the pipettes 40 in place using a pipette holder 5, which may hold the pipette(s) 40 in place prior to establishing a patch clamp configuration and/or before carrying out patch clamp measurements.

FIG. 5C shows an approach that uses hole tapering or inserts to keep the pipettes 40 suspended above the platform 1 (see FIG. 1). A pipette 40 can be inserted into a tapered hole 701. The hole 40 may be of a width such that the pipette 40 cannot pass through the hole without contacting the inner surface of the hole 701, i.e., the inner surface of the pipette holder 7. As a result of the friction between the hole 701 and the pipette 40, the pipette holder 7 may effectively grip the pipette 40 and prevent it from moving vertically through the holder 7. The holder 7 will also prevent lateral motion of the pipette to some extent.

FIG. 4D shows another approach which may utilize the elastic nature of deformable polymer O-rings to hold a pipette 40 in place. Here, the pipette holder 7 may comprise an upper and lower support 704, 705 and an actuator 703 that controls the movement of the supports 704, 705. A pipette 40 is inserted through a hole in an upper support 704 and another corresponding hole in a lower support 705. At the moment shown in FIG. 4D, the pipette 40 is not necessarily held firmly in place. I.e., the pipette 40 may fit loosely inside the upper and lower supports 704,705. In particular, the pipette 40 may not contact the upper and lower O-rings 706, 707 which may be coupled to the upper and lower supports 704, 705, respectively. I.e., the inner diameter 708 of the O-rings may be larger than the diameter of the pipette 40. Thus, in order to keep the pipette 40 in place during this time, a human or other holding means may hold the pipette 40 or otherwise prevent the pipette 40 from sliding through the holes in the supports 704, 705. Alternately, the holes may be of a sufficiently small size that friction between the surface of the holes and the pipette 40 may prevent the pipette 40 from moving vertically.

Once a pipette 40 is in the position shown in FIG. 4D, an actuator 703 may cause the upper and lower supports 704, 705 to move toward each other. The actuator 703 may be motor-driven or pneumatically driven. As the supports 704, 705 are brought together (not shown), upper and lower O-rings 706, 707 may contact each other and compress. Compressing the O-ring may cause the inner diameter 708 of each O-ring to reduce (e.g., the O-rings may flatten). Moving the two supports 704, 705 closer to each other may result in additional O-ring compression and further reduction in the size of the inner diameter 708. The diameter of the O-ring may eventually be reduced so that the O-rings 706, 707 contact and grip the external wall of the pipette 40. At this point, the pipette 40 may be effectively held in place by the O-rings 706, 707.

FIGS. 5C and 5D each show one pipette, and it should be appreciated that the approach shown in the diagrams may be used for any number of pipettes 40. For instance, the pipette holder 5 in FIG. 5C may hold eight pipettes 40 in eight different tapered holes rather than a single pipette 40.

FIG. 6 shows an embodiment of the plexiglass plate 1A, which may be a component of the motor-driven platform 1. The plexiglass plate 1A may be used to support many of the devices necessary to perform patch clamp experiments. In a preferred embodiment of the invention, the motor driven platform 1 is used to support the well plates 3.

FIG. 7 shows an air pressure control system 70 according to an embodiment of the invention. The air pressure control system 70 may comprise (or be coupled to) a data acquisition and control system 25, a pressure regulator/controller 73 (which may be controlled by either a voltage or current input signal, which may be controlled by the control system 25), and an air pressure (+P) and vacuum (−P) source 74 for supplying positive air pressure and negative air pressure to the pressure controller 73, respectively. The air pressure and vacuum sources 74, 75 may be connected to the system 70 via pneumatic tubing (not shown). The pressure controller 73 may be coupled to a positive supply port 76 and negative supply port 77 for receiving the pressure changes from the air pressure sources 74, 75. The pressure controller 73 may further comprise a delivery port 78 for delivering the positive and negative pressure to the pipette 40. In this way, the DAS 25 can control the pressure controller 73 so that it causes a cell 30 to move to the tip of a pipette 40A, burst when it is exposed to air, and then form a gigaseal between the cell membrane 30*a* and the pipette tip 40A (see FIGS. 10A-10C).

The air pressure control system 70 controls the air pressure applied inside the pipettes 40 (not shown). The power and signal of the pressure regulator 73*ay* be controlled by the data acquisition and control system 25. Applying air pressure inside the pipette causes the cells 30 to migrate or flow to the tip of the pipette 40A. As illustrated in FIG. 7, the air pressure may be adjusted by the data acquisition and control system's 25 coordinating software based on measured patch clamp seal resistance. The applied pressures for giga seals range from 0.7 to 3.0 psig.

In one embodiment of the invention, the air pressure control system 70 may be operated as follows. First, a setpoint may be established, e.g., via a visual basic program. The setpoint may be transmitted via the data acquisition and control system 25 to the pressure regulator 73. Second, the pressure regulator 73 may then change its valve position to meet the inputted setpoint pressure, e.g., using an internal proportional, integral, and differential (PID) control loop. Third, a pressure signal may then be transmitted back to the DAS 25 for user feedback. The pressure signal may be measured by the pressure regulator 73. The resistance measurements may be updated, e.g., at a frequency of 1-20 Hz (depending on the computer and DAC 25 performance), and the air pressure may be updated to a new setpoint value, e.g., within 500 milliseconds (or another time period such as one second). These signals may be transmitted using an RS-232 connection, for example.

Various pressure control protocols known in the art may be used for cell 30 placement within the pipettes 40. These may include applying the air pressure in a ramp (continuously increasing) or pulsatile (stepwise increases) fashion.

Figure 8:
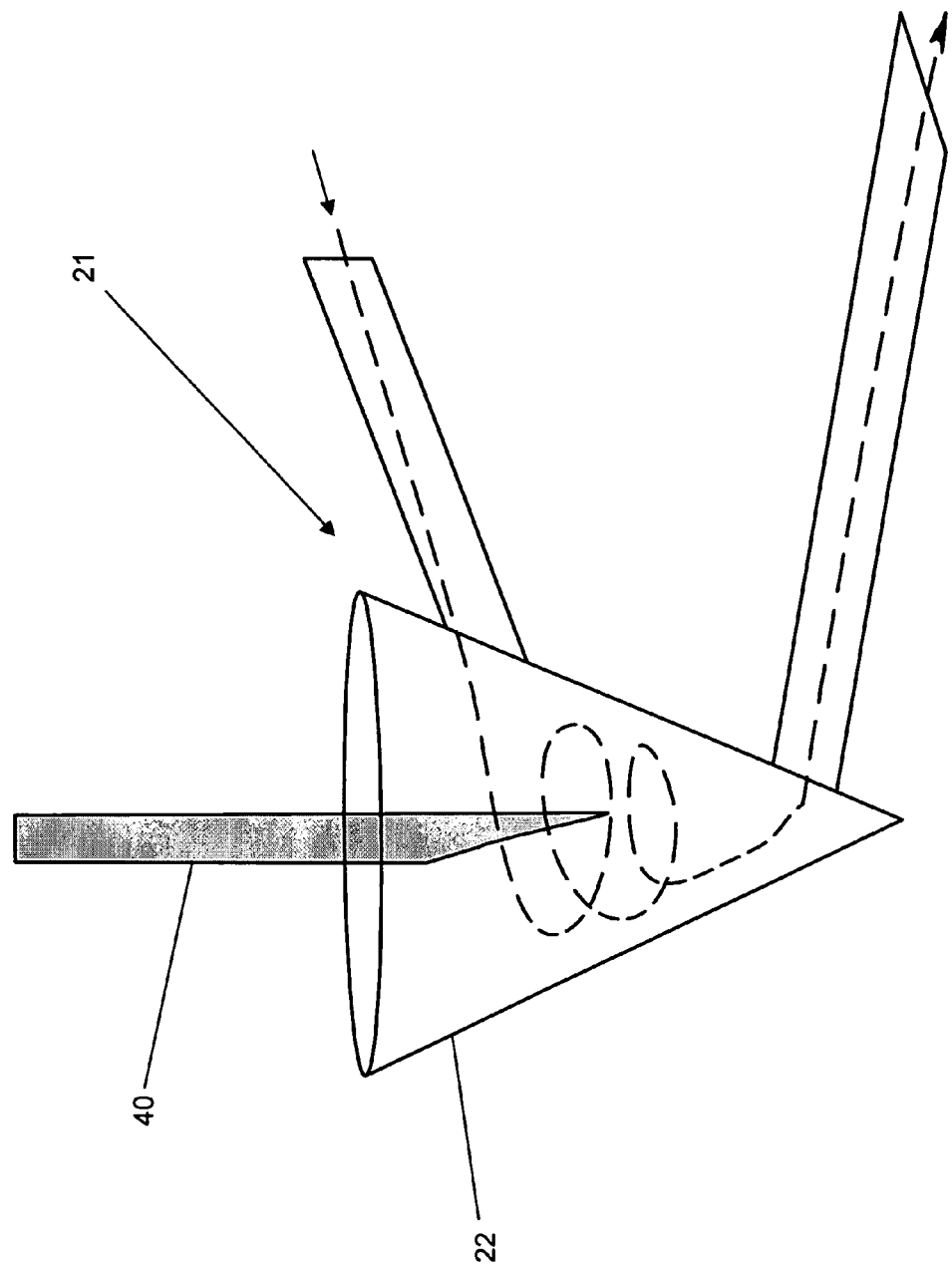
FIG. 8 illustrates an exemplary pipette washing trough.

FIG. 8 shows an embodiment of the fluid wash system 21. In one embodiment of the invention, a separate fluid wash system 21 can be used to wash chemicals away from the cell 30 before or after a patch clamping measurement, e.g., for a cell 30 that will undergo multiple patch clamp tests. FIG. 8 shows a sketch of a pipette washing system 21 in which cones or troughs 22 may be perfused to rinse individual pipettes 40 or rows of pipettes 40. A single cone 22 is shown, although it should be understood that multiple cones could be used. For instance, a row (or series of rows) of cones 22 could enable a row (or series of rows) of pipettes 40 to be washed simultaneously. A pump may be used to perfuse the washing solution into these troughs 22. The helical fluid path shown by the arrow in FIG. 8 may be carefully controlled to ensure minimal cell 30 seal disturbances. Preferably, this fluid path is accomplished by enabling the fluid wash to enter tangential to the circular surface of the pipette. Optionally, internal vanes may be used to direct the fluid motion.

The advantage of the fluid wash system 21 is that it allows more compounds to be tested. Rinsing rows are normally necessary for sufficient rinsing between rows of test compound. However, a fluid wash system 21 would obviate the need for such rinsing rows, thus allowing more rows to be used for testing compounds instead of washing/rinsing.

Figure 9:
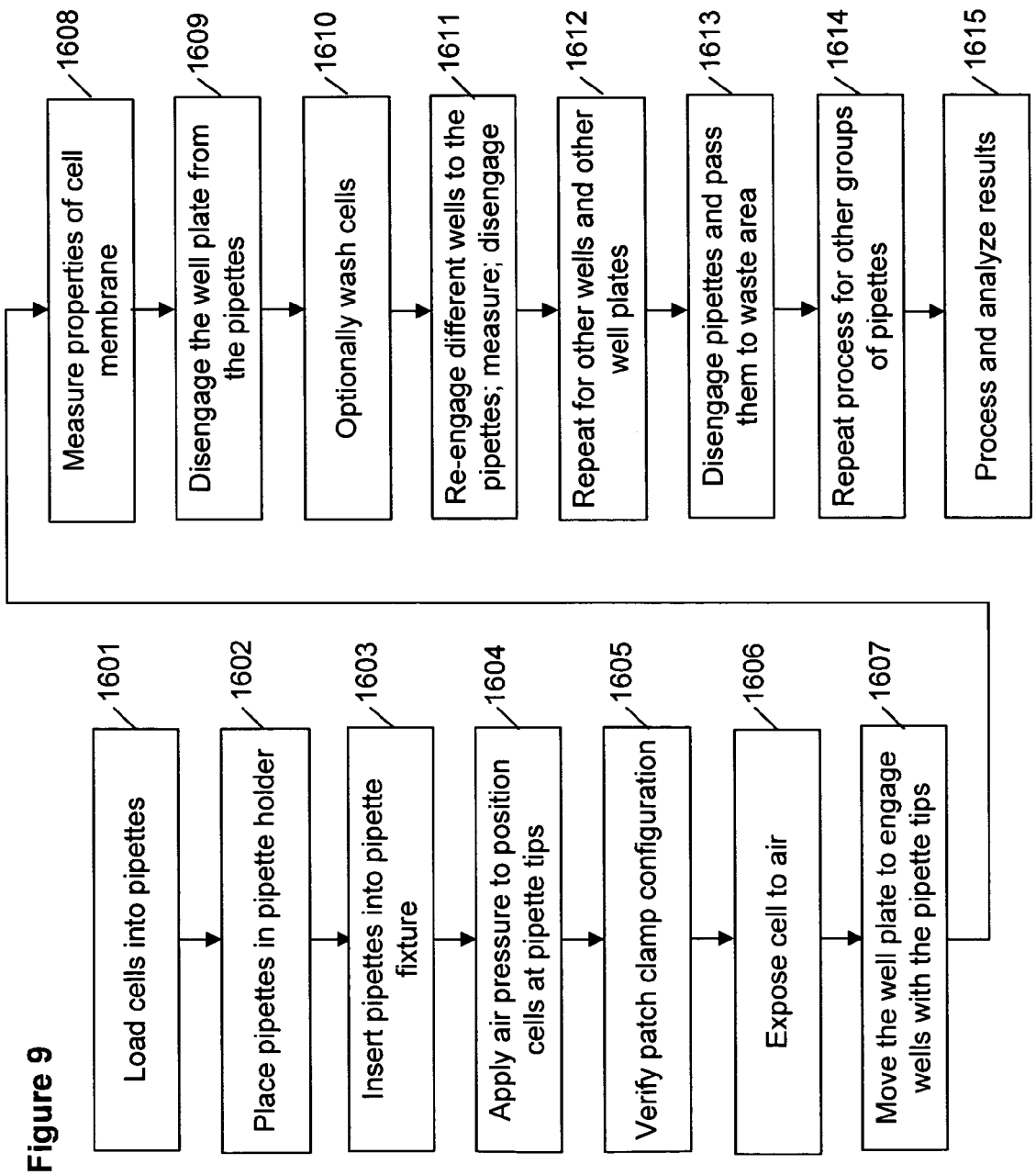
FIG. 9 shows a flowchart illustrating an exemplary method of carrying out patch clamp measurements.
Figure 10:
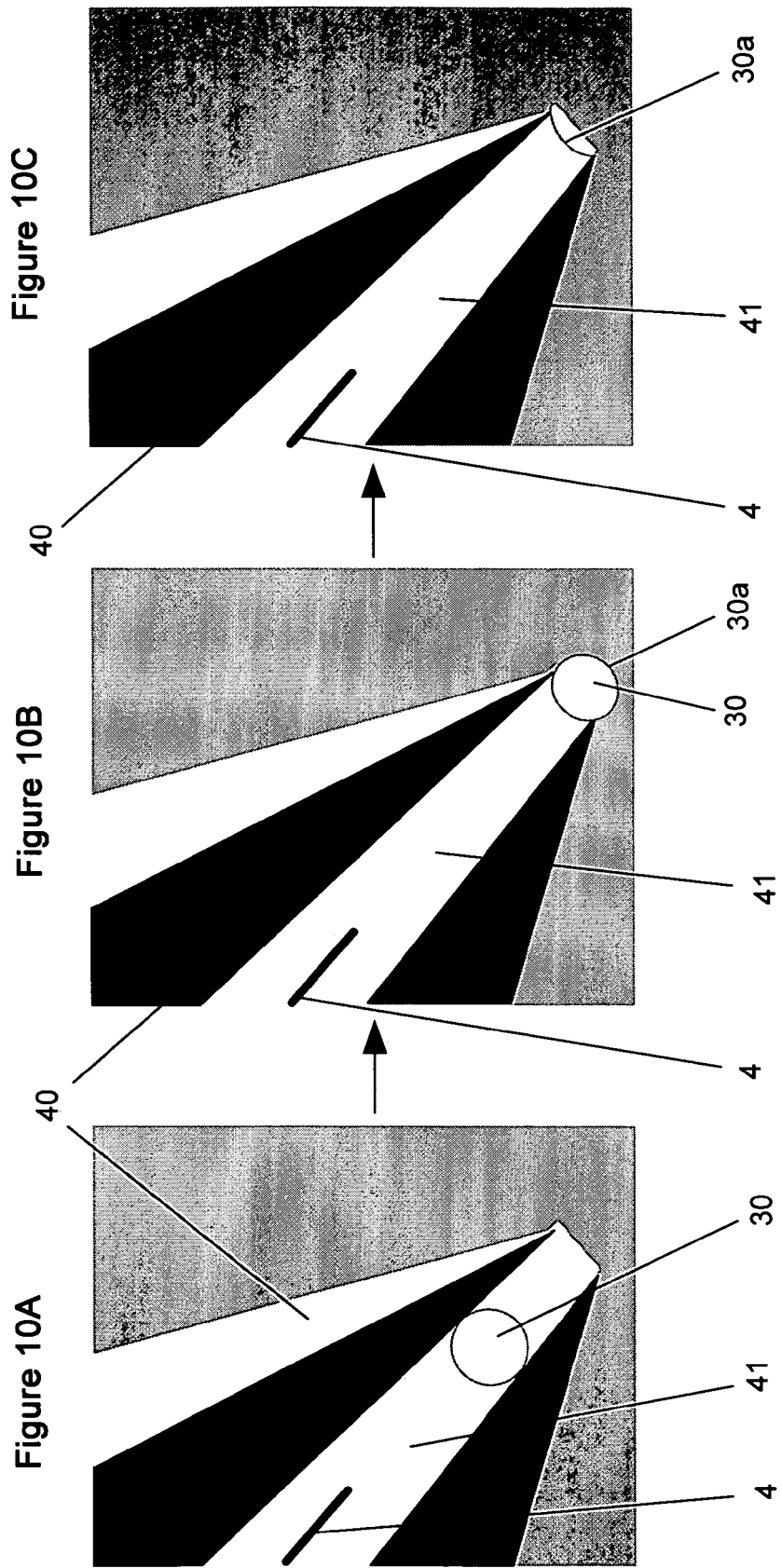
FIGS. 10A-10C show an exemplary process of positioning a cell into an inside-out configuration.

FIG. 9 illustrates a flowchart showing a method of using the system described herein (e.g., in FIG. 1) to measure properties of cells according to an embodiment of the invention. In this exemplary method described in detail below, a patch clamp configuration is established for a plurality of micropipettes. Patch clamp measurements are taken for a plurality of cells while each cell is exposed to a test substance, such as a drug. The pipettes and membranes are washed, and the membranes can then be exposed to other test substances for additional patch clamp measurements.

In step 1601, cells 30 (e.g., CHO-K1 cells) are loaded into pipettes 40. Each pipette 40 has an electrode inside it to be used for patch clamp measurements. Preferably, the cells 30 are loaded by injecting them into the pipettes 40, via a syringe or other means, such as via a small capillary tube, preferably via a WPI, Inc. MicroFil™ capillary needle.

In step 1602, the pipettes 40 are placed in a pipette holder 7, which is located on a moveable platform 1. For instance, eight pipettes 40 may be placed in a row in the pipette holder 7. The platform 1 also holds one or more multi-well compound plates 3, each containing test compounds, control substances, or washing solutions.

It should be noted that the cells 30 may be loaded into the pipettes 40 after the pipettes 40 are placed in the pipette holder 7.

In step 1603, the platform 1 is moved relative to a pipette fixture 5 so as to stably attach the pipettes 40 (such as a plurality of pipettes arranged in a row or other arrangement) to the pipette fixture 5. The platform may be first moved to line up the pipette holder 7, in which the pipettes 40 are held in place, with the pipette fixture 5. In this step, the pipette holder 7 may first be moved into a position directly beneath the pipette fixture 5. Then, the platform 1 may be moved upward toward the pipette fixture so that the pipettes 40 held by the pipette holder 7 are stably attached to the pipette fixture 5. The pipette fixture 5 may comprise a coupling device for coupling the pipettes 40 to the pipette fixture 5.

The pipette holder 7 may then be disengaged from the pipettes 40 so that the pipettes 40 are coupled only to the pipette fixture 5. In a preferred embodiment, the pipettes 40 are stably suspended from the pipette fixture 5 in a substantially vertical orientation so that the pipette tip 40A faces in a downward direction, e.g., toward the floor.

In step 1604, air pressure is applied inside the pipettes 40 by the air pressure control system 21 and causes each cell 30 to move through the pipette 40. One method of accomplishing this step is described herein with respect to FIG. 7. In a preferred embodiment, the cell 30 will eventually reach the tip 40A of the pipette 40. During this step 1604 an appropriate seal is established between the pipette tip 40A and the cell membrane 30A, e.g., a giga-ohm seal. When the seal is established between the pipette tip and the cell (or portion thereof, such as a membrane), the cell and pipette are considered to be in a patch clamp configuration. At the pipette tip 40A, the cell 30 may be exposed to ambient air, and as a result a portion of the cell wall 30A may spontaneously rupture, creating an "inside-out whole-cell" configuration (see FIGS. 10A-10C).

Typical pressures used for positioning the cell 30 are 0.7 to 3 psig. This step 1604 preferably takes between 2 and 60 seconds, more preferably between 5 and 15 seconds. Once a cell 30 is in position at the pipette tip 40A, the pressure inside the pipette 40 may be changed to 0.0 psig (which may indicate zero differential pressure between the inside of the pipette and the pressure outside the pipette. The pressure inside the pipette may also be changed to 0-1 psi positive differential pressure. Some positive pressure might be needed to ensure seal stability.

Instead of applying air pressure, other means of attaching a cell 30 to a pipette tip 40A may be used, such as those disclosed in the applications discussed above. Also, other types of cell configurations can be achieved besides an inside-out whole cell configuration. For instance, if the tip of the pipette 40 is exposed to a saline or another solution rather than air, then the cell 30 may not rupture, and the cell 30 may instead be in a position for other types of patch clamp measurements.

In step 1605, the patch clamp configuration may be verified for one or more pipettes 40. For instance, resistance measurements may be taken to verify that a proper seal has formed between the membrane 30A and the pipette tip 40A of a pipette 40, e.g., a gigaseal. When the patch clamp configuration is verified, the membranes 30A are ready for patch clamp measurements, such as inside-out whole-cell patch clamp measurements. The seal may be continuously monitored throughout the various subsequent steps of the method described herein.

In step 1606, the cell may be exposed to air. For instance, the cell may be at the tip of the pipette, and the portion of the cell membrane that is not facing the inside of the pipette or touching the pipette walls may be exposed to ambient air. This step 1606 may occur as described for FIG. 10C (see FIGS. 10A-10C). Upon exposure to air, the cell membrane may rupture, and the cell may then be in an inside-out whole cell patch clamp configuration. It should be noted that the patch clamp configuration may be verified in step 1605 after cell rupture instead of before.

In step 1607, the well plate 3 and pipette fixture 5 may be relatively moved so that the membranes 30A, which are located at the tips 40A of the pipettes 40 held in place by the pipette fixture 5, are inserted into one or more first substances contained in the first wells 3A of the well plate 3. The substances in the wells 3A may comprise drugs of varying concentrations, saline solutions, washing solutions, control substances, or other chemicals. For instance, one well may contain one drug solution, and another well may contain a similar solution but with a different concentration of the drug. Preferably, each of the first wells 3A contains an identical substance.

Each substance in the wells 3A is preferably in electrical contact with a reference electrode 45 coupled to a measuring device, such as the head stage electronics 18. For instance, the reference electrode 45 may be inside the well 3A and in physical contact with the test solution. In this way, the reference electrode 45 may conduct electrical current that passes through the substance and the membrane 30A for purposes of patch clamp measurement.

During this step 1607, the membranes 30A should be in contact with both the substance and an electrode by virtue of the well 3A, and the membranes should also be in contact with another electrode 4 located inside the pipette 40. The electrode 4 may also be elsewhere inside the pipette 40 (such as in the main body of the pipette), according to traditional patch clamp techniques.

In step 1608, electrical properties of the membrane 30A are measured. For instance, patch clamp measurements are taken for the membranes 30A while they are in contact with the first substances in the first wells 3A. In this way, the effect of the first test substance(s) on the ion channels of the membrane(s) 30A may be measured, for example.

In preferred embodiments one or more of the following parameters (e.g., electrical properties) may be measured in the cell 30: current across one or more electrodes and/or across the cell 30 or cell membrane 30A, voltage across the electrodes and/or across the cell 30 or cell membrane 30A, electric resistance, impedance, optic fluorescence, plasmon resonance, mechanic resonance, fluidity and/or rigidity. Proteins expressed in the cell membrane will be subject to the applied electrical, mechanical, etc. forces, and thus may be altered in their conformation.

In step 1609, the pipette fixture 5 and well plate 3 are relatively moved so that the first wells 3A are disengaged from the pipette tips 40A (and membranes 30A therein). For instance, the well plate 3 can be moved in a downward direction away from the pipette fixture 5 while the pipette fixture 5 (and pipettes 40 stably attached thereto) remain in place. Alternately, the pipette fixture 5 may be moved upward and away from the well plate 3, achieving the same result.

In step 1610, the membranes 30A and/or pipettes 40 are optionally washed. The washing step 1610 may take place at this point in the process or at any other time after a patch clamp measurement. Preferably washing is performed 2 to 5 times, such that any test substance that remains in the fluid surrounding the membranes 30A is ultimately diluted below its level of activity on the membrane 30A.

In one embodiment, the pipettes and a fluid wash system 21 may be relatively moved so that the pipette tip 40A is inside the fluid wash system 21, as shown in FIG. 8. Fluid may then be passed over each pipette tip 40A and corresponding membrane 30A. A plurality of pipettes 40 may be washed simultaneously using a plurality of fluid wash systems 21, or each pipette 40 may be washed individually in sequence using a single fluid wash system 21.

In another embodiment, the membranes 30A and/or pipette tips 40A are washed by inserting them into a well 3A that contains wash fluid. The wells 3A containing the washing fluid may be adjacent to the wells 3A containing the first substance(s). For instance, the washing fluid may be in one or more rows of wells 3A adjacent to the row of wells 3A containing the first test substance. After the patch clamp measurement in step 1608, the row of pipette tips 40A may be inserted into 2-5 rows of wells 3A containing washing fluid, resulting in 2-5 washings. Such positioning of substances and washing fluid minimizes the activity and time required to move and wash the pipette tips 40A.

After washing, the pipette tips 40A can be removed from the fluid wash system 21 or washing wells 3A. The pipettes 40 are then ready for an additional patch clamp measurement. If the membrane 30A is to be moved from wells 3A containing lower concentrations of a test substance to wells 3A containing higher concentrations of a test substance, the washing step 1610 may be eliminated according to standard laboratory practice.

In step 1611, steps 1607-1609 are repeated for a second set of wells 3A containing a second set of substances. I.e., the pipette tips 40A (and membranes 30A contained therein) and a different set of wells 3A are relatively moved so that the pipette tips 40A are in contact with second substances contained in the wells 3A. One or more patch clamp measurements are taken, and the membranes 30A are again removed from the substances by relatively moving the pipette fixture 5 and well plate 3 so that the pipette tips 40A are removed from the wells 3A. Preferably, the second set of wells 3A is different from and adjacent to the first set of wells 3A (or adjacent to the washing wells 3A of step 1610). Alternately, in another embodiment, the membranes 30A are re-engaged with the same set of wells 30A in this step 1611.

In step 1612, additional patch clamp tests may be conducted on the same or different membranes 30A. For instance, steps 1607-1609 may be repeated for the pipettes 40 for a third row of wells 3A containing a third set of test substances. The test substances may comprise different drugs or different concentrations of previously tested drugs.

Also, different pipettes 40 (such as a different row of pipettes) can be used to conduct one or more series of patch clamp measurements and/or washings, using the same or different wells 3A. This process is repeated as many times as desired. In this way, a plurality of patch clamp measurements can be taken for a plurality of membranes and a plurality of drugs (or drugs of varying concentrations). A single cell 30 can be used for a variety of measurements.

In step 1613, the pipettes 40 are disengaged from the pipette fixture 5. The pipettes may be passed (e.g., dropped) to a waste area or receptacle 49. For instance, upon completing the patch-clamp testing with one row of pipettes 40, the pipettes 40 may be disengaged from the compound plate 3 by moving the platform 1 away (e.g., downward) from the pipette fixture 5. The pipettes 40 may then be disengaged from the pipette fixture 5 by providing a pulse of high pressure to the row of pipettes 40, expelling them into the disposal area 49. Alternately, a device coupling the pipettes 40 to the pipette fixture 5 may disengage the pipettes 40, causing them to pass to the disposal area 49.

In step 1614, the entire process may be repeated for another set (e.g., row) of pipettes 40 and cells 30. The process may repeat beginning at step 1601, 1602, or 1603, depending on whether the second set of pipettes 40 have been loaded with a cell 30 and whether the pipettes 40 have been placed in a pipette holder 7.

In step 1615, the results of the patch clamp measurements are processed at the data acquisition and control system 25. The results may be processed at any time, such as at the time of each measurement. Analysis may be conducted using various commercial software products, such as Pulsefit or Origin 7.

Other methods can be considered, such as those otherwise disclosed herein.

It will be understood that it is not necessary to use all of the pipettes and wells. Some wells and pipettes may remain empty for a series of patch clamp measurements. In one embodiment, the method uses only one pipette and one well. Similarly, it should be recognized that while the above described steps embody a preferred method of using the apparatus, one skilled in the art may add or delete steps to suit a particular application.

Preferably, the methods according to the present invention utilize multiple recording elements that are multiplexed to a data-acquisition apparatus by multiple voltage-clamp amplifiers. Such amplifiers can also be used in current-clamp, or phase-locked amplifier mode. This arrangement provides extremely high time-resolution, and allows virtually simultaneous measurements from all wells.

Preferably, the methods of the invention utilize very small volumes of test compounds. Less volume means that less compound needs to be washed before a subsequent test, so less washing is required.

Preferably, the methods are performed in temperature- and atmosphere-controlled environments. This allows for a more accurate approximation of the physiological buffers, gas exchange, and temperatures conducive to studying the cells 30.

A variety of different cell types can be examined with the present system. A non-exhaustive list of some of the cells that can be examined include: Jurkat lymphoma cells; HEK293 cells; Chinese hamster ovary (CHO) cells (e.g., ion channel/transport protein containing cell lines); primary cells from neuronal tissue such as hippocampus, cortex, brain stem, thalamus, amygdala, hypothalamus, midbrain, spinal cord, and other CNS neurons, ganglion neurons, dorsal root ganglion neurons, and neuroendocrine cells; skeletal muscle; smooth muscle; heart muscle; immune cells; blood cells; epithelia; endothelia; plant and genetically engineered cells. In a preferred embodiment of the invention, the cell 30 sealed to the pipette 2 and being tested is an animal cell. The cell 30 may be a mammalian, insect, or amphibian cell. More preferably, the cell 30 contains an ion channel or transport protein in its cell membrane 30A, either naturally or introduced artificially by well known molecular biological techniques. Even more preferably, the cell 30 is a mammalian cell such as a human cell.

FIGS. 10A-10C show the process of positioning a cell 30 in an inside-out patch clamp configuration according to an embodiment of the invention. FIGS. 10A-10C show a pipette 40 and a cell 30, as the cell 30 is moved into a position for patch clamping within the pipette 40. The cell 30 may begin in a position somewhere in the interior of the pipette, as shown in FIG. 10A. For instance, an undisturbed cell 30 may be loaded into the interior of the pipette 40 through the wider top portion of the pipette 40. Once the cell 30 reaches the tip and is configured properly (e.g., the cell membrane 30A forms a giga-ohm seal with the pipette tip 40A), exposure to ambient air causes spontaneous cell rupture, as shown in FIG. 10C.

FIG. 10A shows the cell 30 in an interior position in the pipette 40. The air pressure control system 70 may apply air pressure to the cell 30 or fluid 41 in the pipette 40 and thereby cause the cell 30 to move downward toward the pipette tip 40. Gravity may help this process.

As shown in FIG. 10B, the cell 30 eventually reaches the tip of the pipette 40. In this position, the cell is exposed to the ambient air, which causes the exposed cell membrane 30A to rupture.

As shown in FIG. 10C, the rupture cell 31 results in an inside-out whole-cell configuration, which will remain at or near the tip of the pipette 40. Here, the ruptured whole cell 31 is inside the pipette 40, and a portion of the inner part of the cell membrane 30A is exposed at the tip of the pipette 40 facing outward away from the pipette 40. A suction may be applied inside the pipette 40 to create a giga-ohm seal (also called a gigaseal) between the cell membrane 30A and the pipette tip 40A, although a suction is not necessary. The ruptured cell 31 is then ready for inside-out whole cell patch clamp measurements across the portion of its membrane 30A exposed at the tip 40A of the pipette 40.

Figure 11:
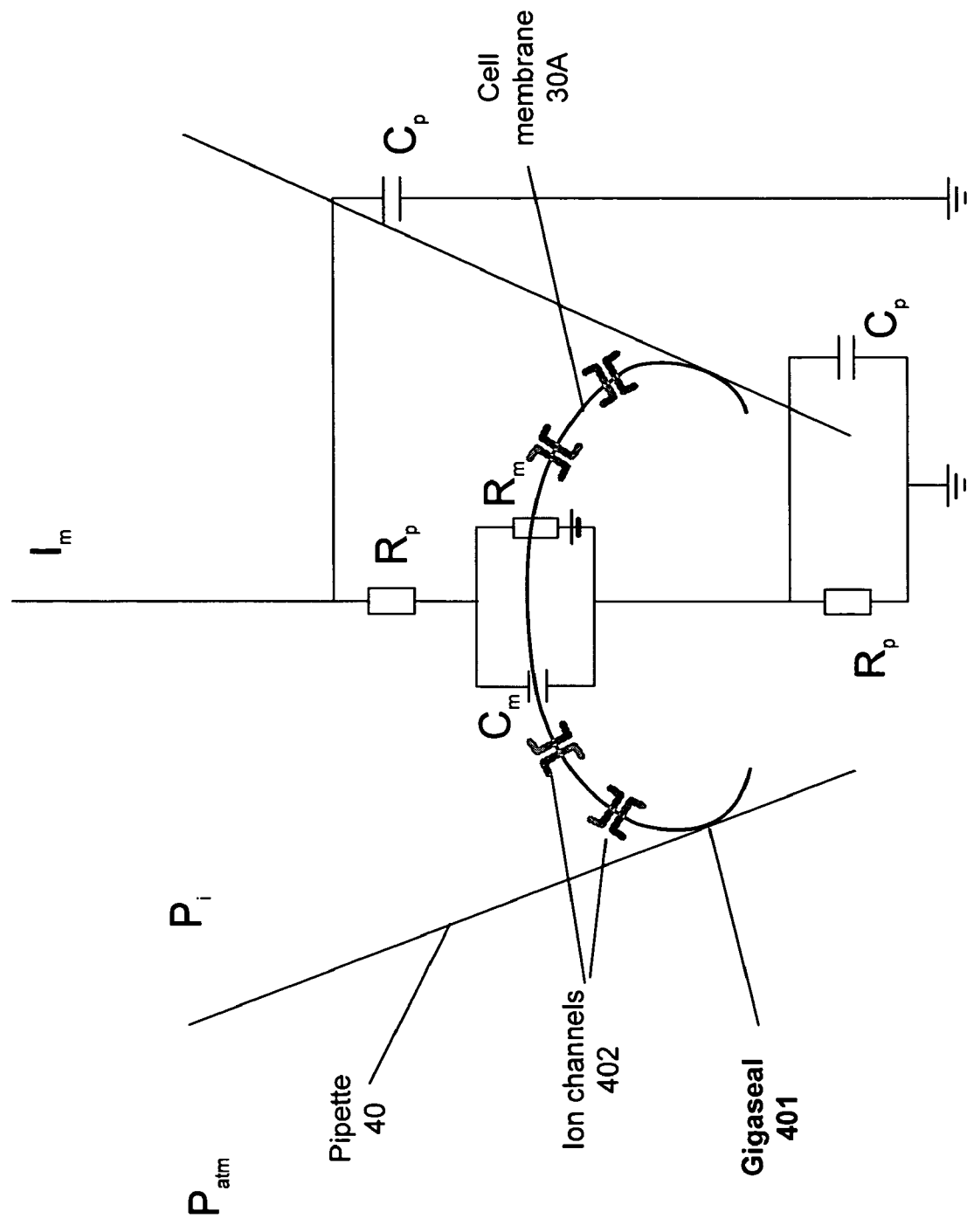
FIG. 11 illustrates an exemplary equivalent electronic circuit of the "inside-out" whole-cell patch.

FIG. 11 illustrates an equivalent electronic circuit of the "inside-out" whole-cell patch according to an embodiment of the invention. The configuration has this name because the whole cell 30 is located within the pipette 40 with the inside part of the cell 30 membrane 30A facing outward.

The electronic circuit may comprise any typical electronic circuit that is used for making patch clamp measurements. Here, a HEKA EPC9/2 amplifier may be utilized.

A gigaseal 401 is formed between the cell 30 and the pipette 40. Because of the seal 401, the pressure ($P_i$) inside the pipette 40 may be different from the pressure ($P_{atm}$) outside the pipette 40, which is typically the atmospheric pressure. A different relative pressure $P_i$ inside the pipette 40 compared to outside may create the gigaseal. The ion channels 402 reside along and across the membrane forming the gigaseal 401.

The circuit diagram shows connections between the resistors and capacitors that form the basic patch clamp measurement circuit. Current (I) and voltage (V) can be measured in the circuit. The measured current is typically the current flowing through one or more ion channels 402.

EXAMPLES

Results Obtained Using Method of Invention

Several experiments were conducted using the method described herein. Ion channel results are shown in FIGS. 12-17.

Figure 12:
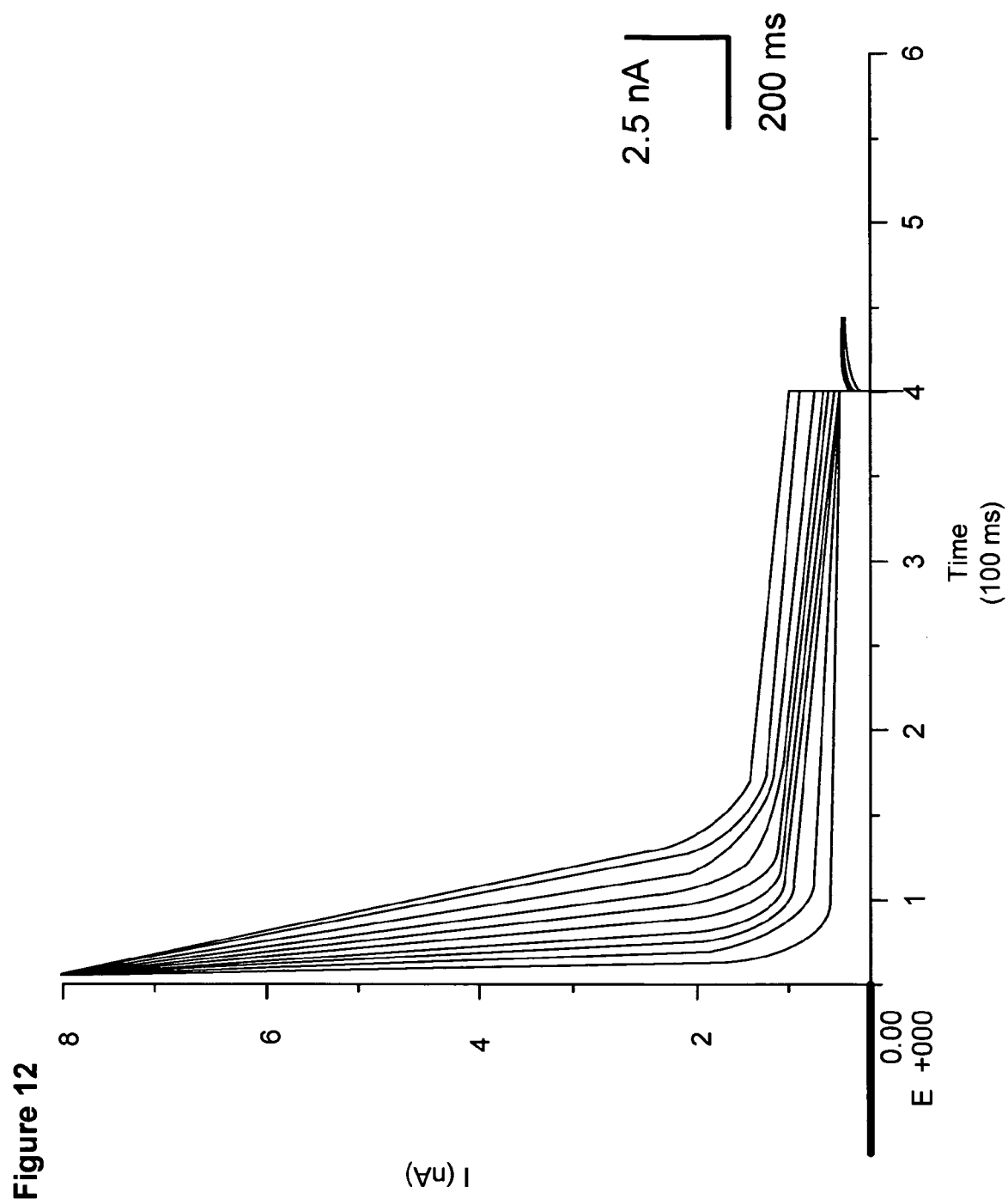
FIG. 12 illustrates a graph showing potassium currents of an exemplary inside-out patch clamp configuration showing the effect of 4-AP and a wash-out.

FIG. 12 shows the outward potassium currents for a single pipette and a single cell according to an embodiment of the invention. These currents were elicited by a test voltage of +40 mV preceded by a 500 ms long prepulse to –110 mV from a holding potential of –70 mV. The lack of signal noise found in FIG. 12 shows a high quality signal. Current traces were obtained in 5 minute time intervals.

Figure 13:
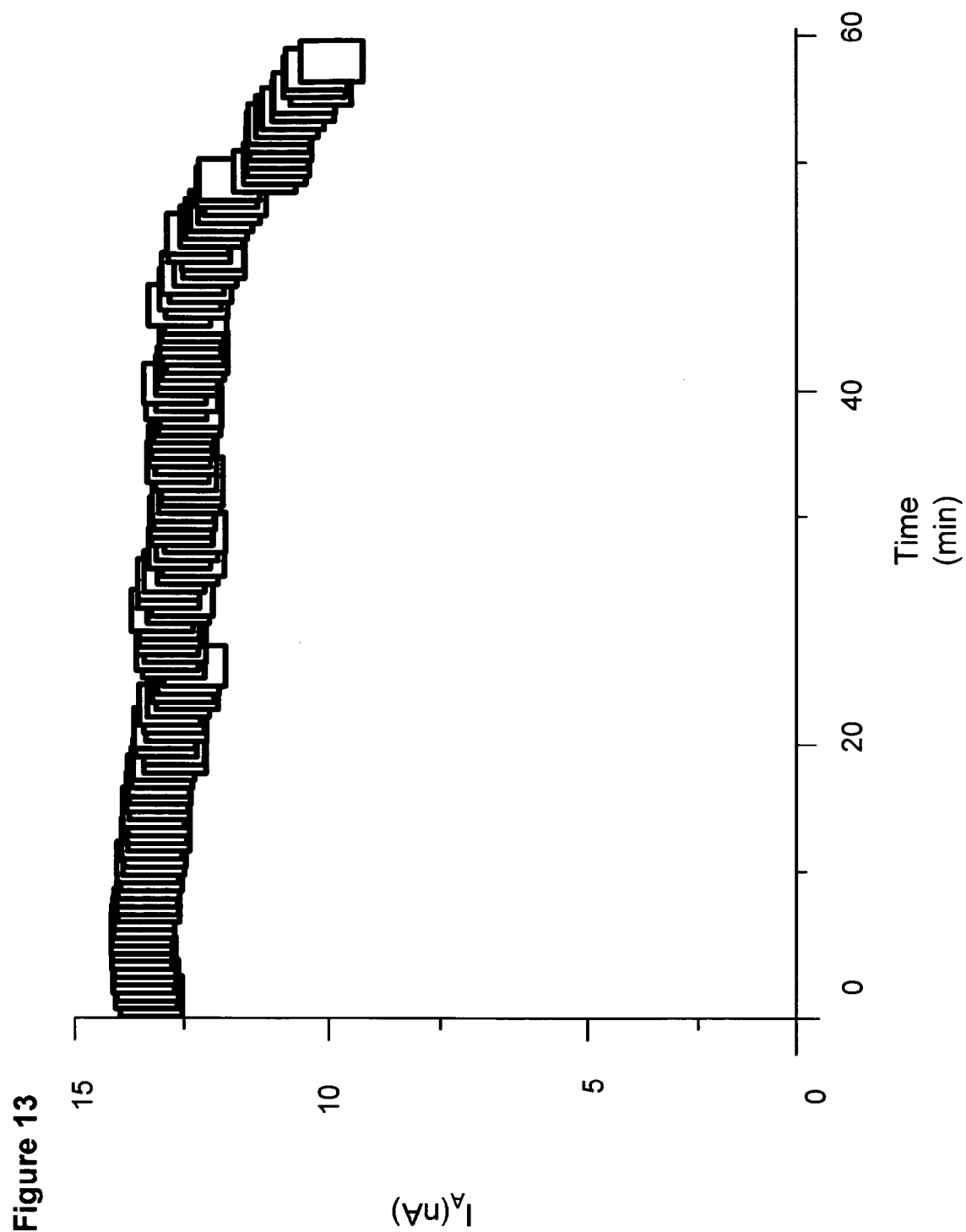
FIG. 13 illustrates a graph showing a stable peak current amplitude of an exemplary inside-out patch clamp configuration.

FIG. 13 illustrates a graph showing a stable peak current amplitude according to an embodiment of the invention. The peak current was measured for a single pipette and a single cell according to the setup used in FIG. 12. As shown in FIG. 13, the peak current remains relatively stable (near 13 nA) throughout many measurements. Having stable peak current measurements enables researchers to clearly distinguish between drug effects and poor patch clamp configurations. Most patch clamp protocols call for only 10 minutes of relatively stable measurements per compound concentration tested. As shown in FIG. 13, the peak current in an embodiment of the invention remained very stable (near 13 nA) for over 40 minutes, with only a slight (5-10%, 0.5-1 nA) decrease over the next twenty-thirty minutes.

FIGS. 14-17 demonstrate the rapid onset and wash-out characteristics of a system according to an embodiment of the invention. These characteristics are consistent with the high diffusion rate of "inside out" whole cell configurations. Two representative experiments are shown in FIGS. 8-11.

Figure 14:
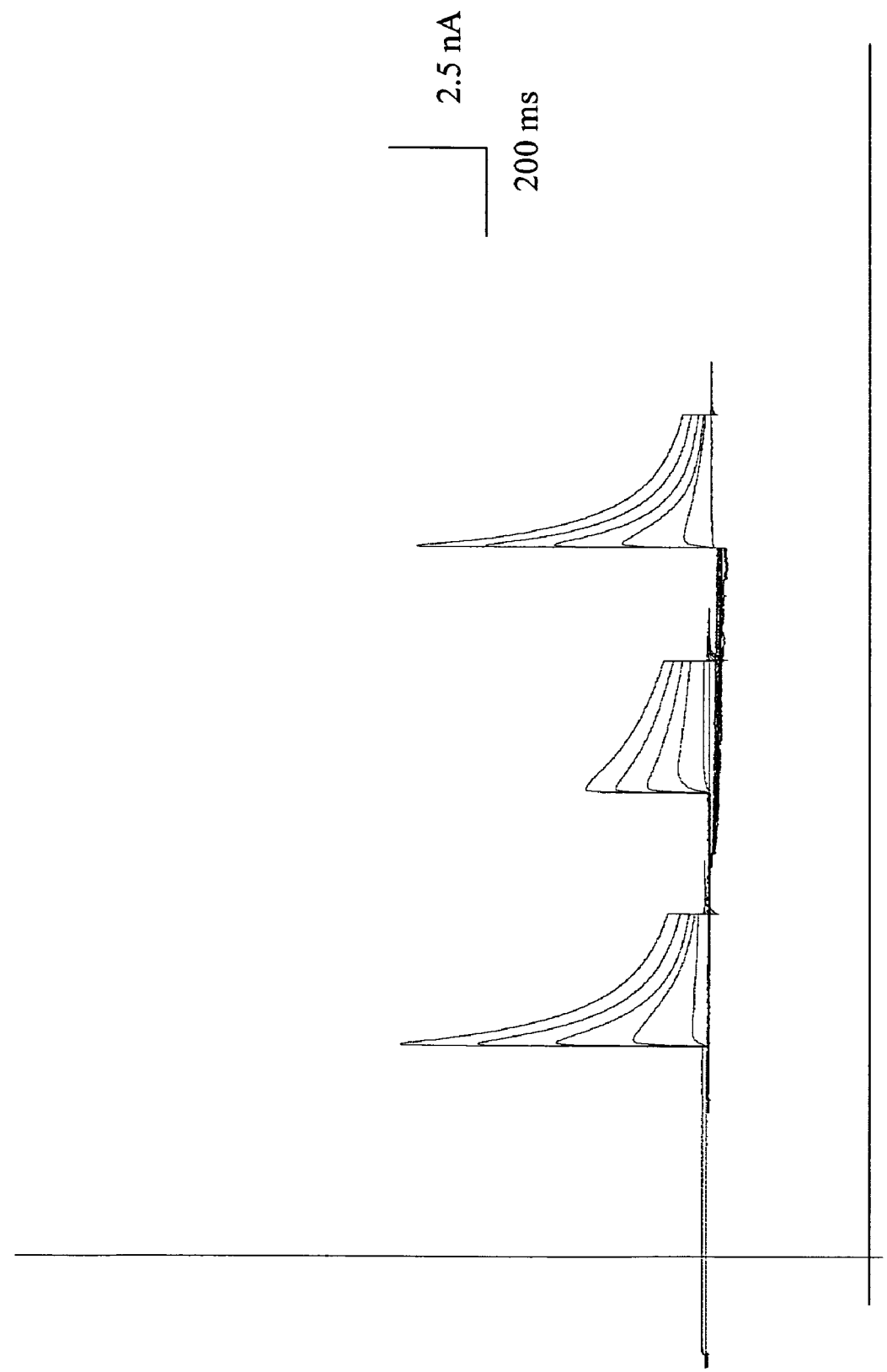
FIG. 14 illustrates a graph showing outward potassium currents of an exemplary inside-out patch clamp configuration with test compounds.

FIG. 14 illustrates a graph showing outward potassium currents with test compounds according to an embodiment of the invention. Specifically, FIG. 14 shows the outward potassium currents for the first cell in a single pipette for 0.5 second test pulses ranging from –60 mV to 40 mV in increments of 20 mV. Each test increment followed a 0.5 second long hyperpolarizing prepulse to –110 mV, while keeping the membrane potential at –70 mV between pulses. In the first (left-most) plot, measurements of current were taken while the cell was bathed in a control solution. The cell was then placed in a 10 mM 4-AP bath solution, and the measurements of the second (middle) plot were recorded. The chemical called 4-AP is a pharmacological blocker of these ion channels. The cell was then washed of the 4-AP solution, and the cell was again bathed in the control solution. Measurements were recorded as in the first and second plots, and the results are shown in the third (right-most) plot. For purposes of an inside-out whole cell patch clamp measurement, the control and 4-AP baths represented the intracellular region.

The results shown in FIG. 14 demonstrate that a 10 mM 4-AP bath solution, representing the intracellular region, blocked the potassium current amplitude by about 50% (see center plot compared with first and third plots). These results also show that the effect is fully (or at least substantially) reversible with wash-out perfusion, as the results after washing (shown in the right plot) are nearly identical to the results obtained under the initial control circumstances, before application of the 4-AP bath.

Figure 15:
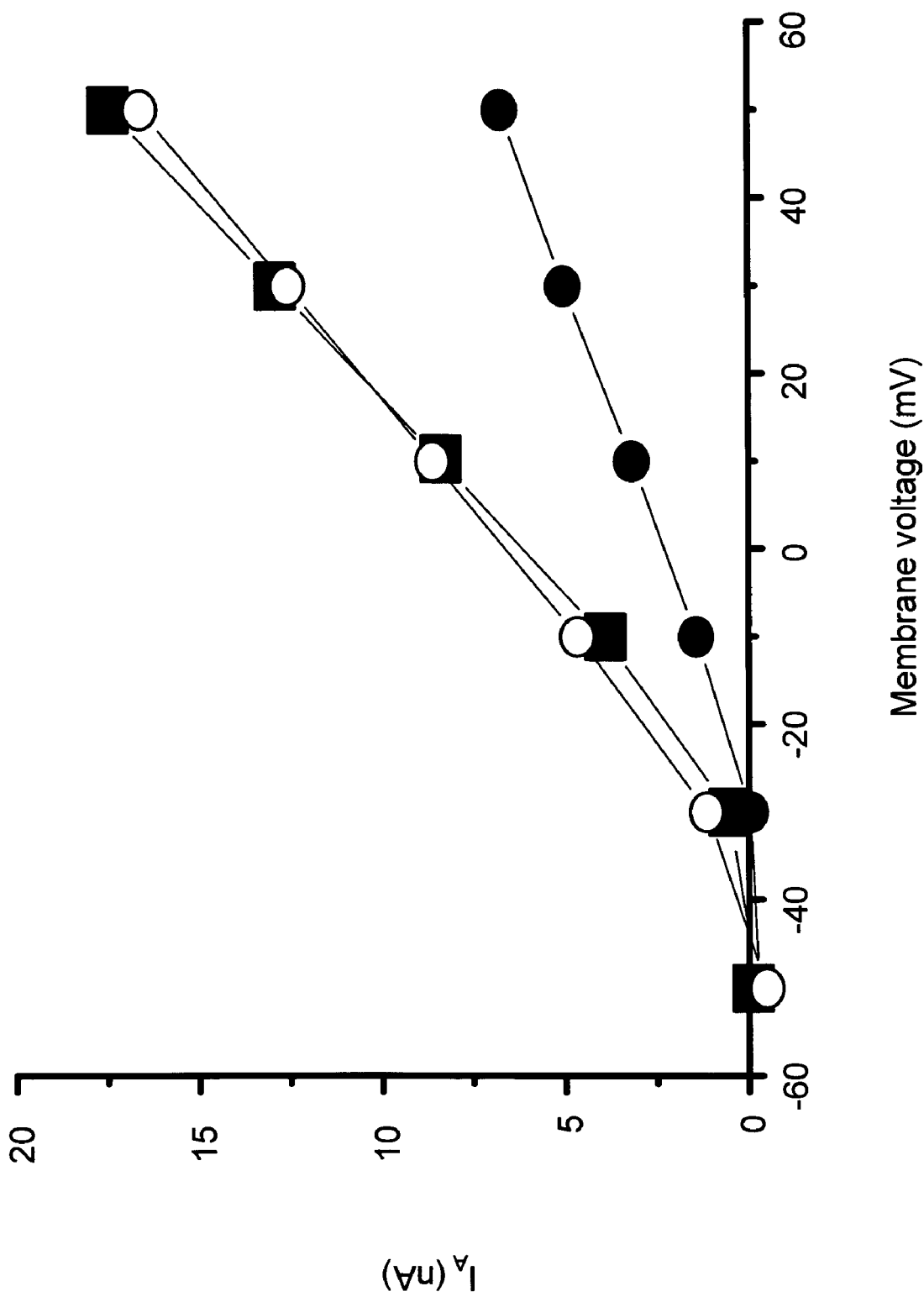
FIG. 15 illustrates a graph showing a potassium current amplitude behavior of an exemplary inside-out patch clamp configuration as a function of applied membrane voltages.

FIG. 15 illustrates a graph showing potassium current amplitude (I) behavior as a function of applied membrane voltages (V) according to an embodiment of the invention. These results show the results of FIG. 14 in a current amplitude versus membrane voltage plot. Here, the black square points correspond to the left-most plot in FIG. 14, the black circles correspond to the center plot of FIG. 14 showing the reduced potassium current in the presence of 10 mM 4-AP bath solution, and the white circles correspond to measurements after the 4-AP was washed away in the right-most plot of FIG. 14. As shown in FIG. 15, the current across the membrane when the cell was in the 10 mM 4-AP bath solution (indicated by solid black circles) was less than 50% of the current when the cell was in the control solution. Further, the measurements using the control solution after washing (indicated by white circles) is nearly identical to the results obtained before varying the bath (indicated by solid black squares), indicating a reversible process wherein washing the chemical successfully returns the cell to its prior state.

Figure 16:
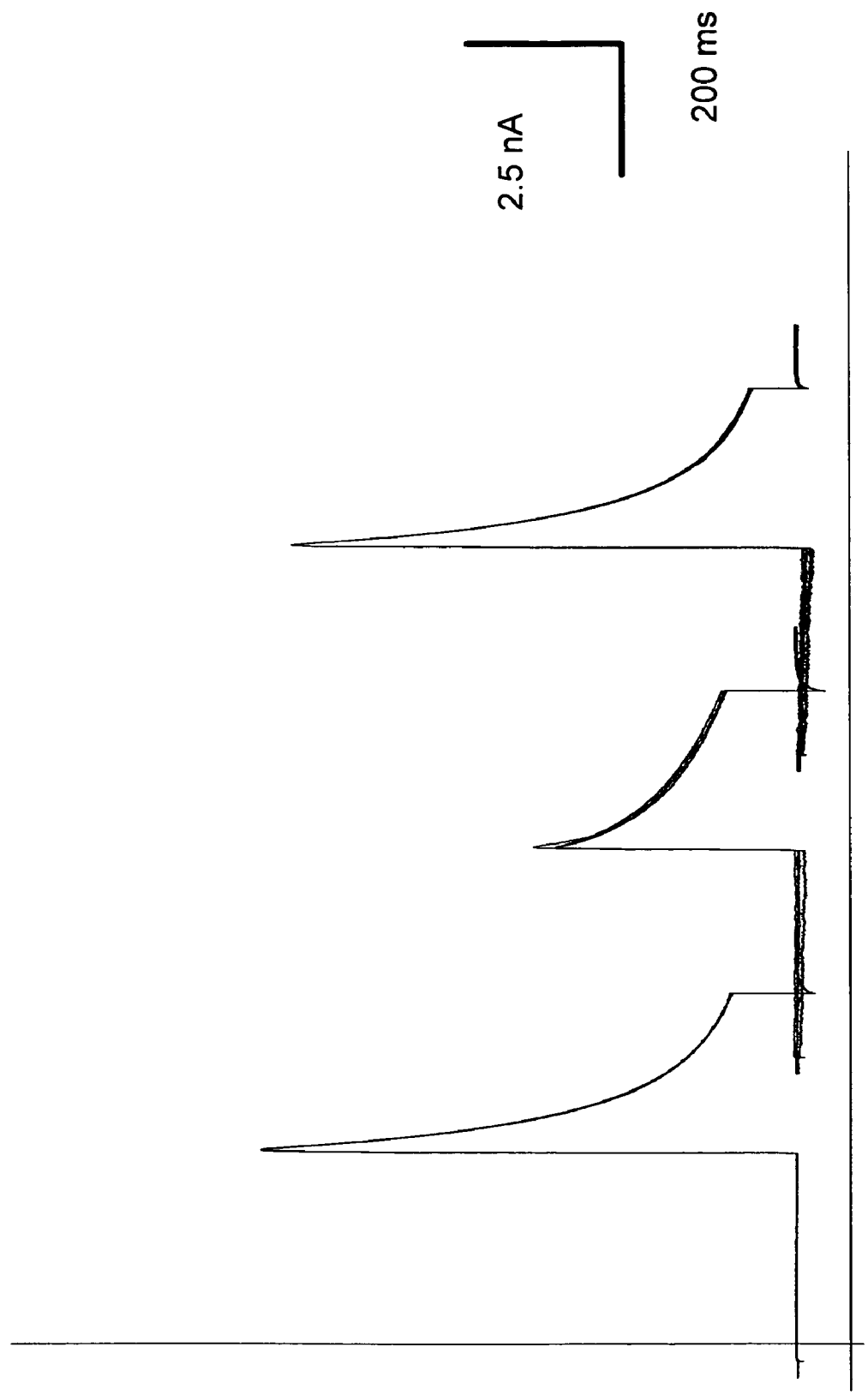
FIG. 16 illustrates a graph showing a potassium current behavior of an exemplary inside-out patch clamp configuration with the chemical 4-AP.

FIG. 16 shows the behavior of the second cell. FIG. 16 demonstrates the pharmacological block of ion channels in the second cell membrane by 4-AP, much like the same block is shown for the first cell in FIG. 14. The middle plot shows measurements taken in the presence of 4-AP. The middle plot shows current during the action of the drug 4-AP. This current is approximately 50% lower than in the left and right plots, which correspond to measurements in the control solution before and after drug action, respectively. The analysis of current versus time for this data is shown in FIG. 17.

Using high-quality pipette glass electrodes, a 70-80% success rate (true gigaseal and subsequent whole-cell formation) was routinely observed for numerous cell lines, including CHO-K1, U937 and HEK293. While many other systems have been automated, the seal quality has yet to be clearly stated in the literature. The system of the present invention allows the testing of hundreds of cells each day.

Figure 17:
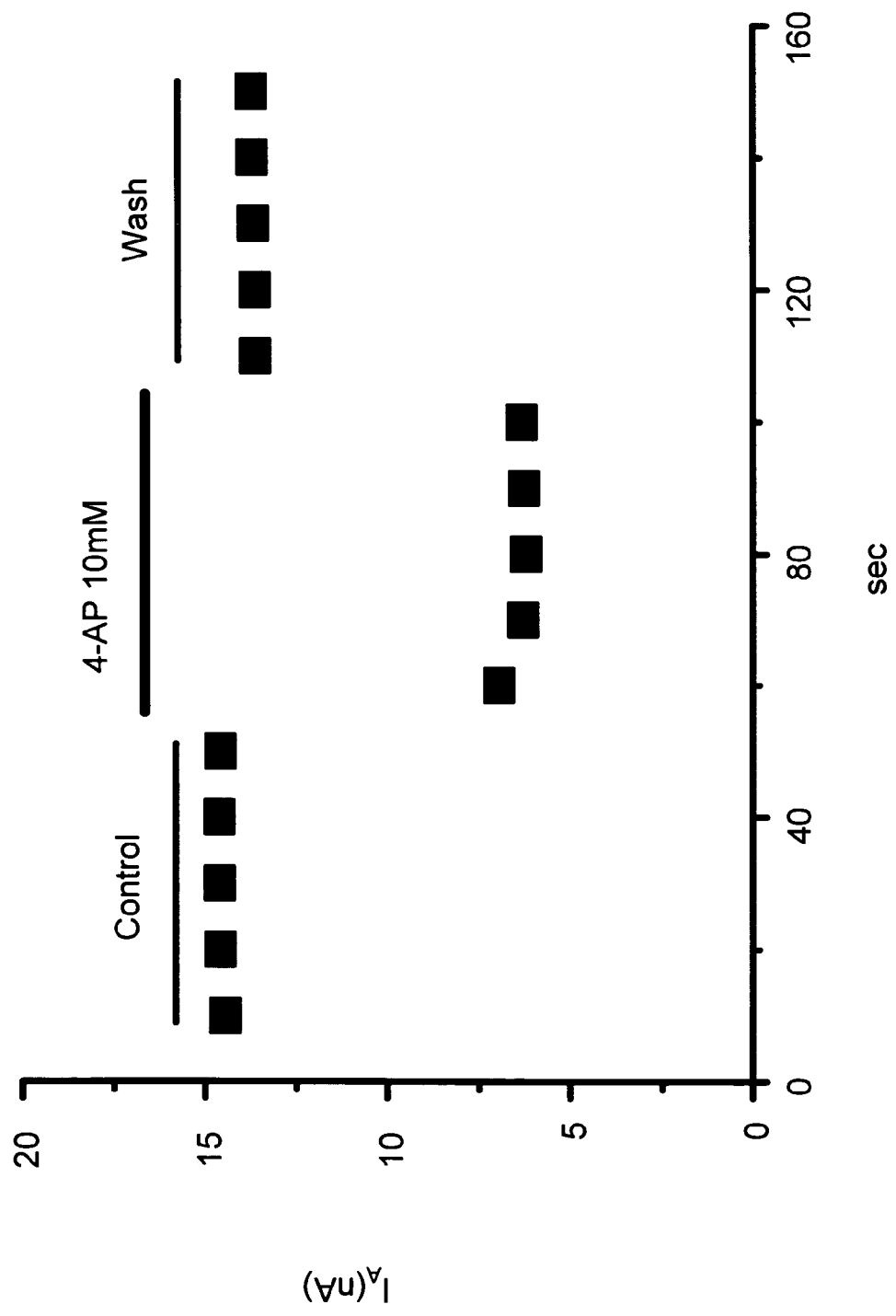
FIG. 17 illustrates a graph showing a potassium current amplitude time trace of an exemplary inside-out patch clamp configuration.

FIG. 17 demonstrates the wash-out ability of the system, showing the current amplitude before, during, and after drug action, again corresponding to the left, center, and right plots. The results show that the measurements taken after washing (right-most data set) are nearly equal to the measurements taken when the cell was exposed to the control substance.

Measurements were taken in ten second intervals, and the measurements were very consistent for each test substance. Thus, only 10 second intervals are required to return to various steady-state levels, again demonstrating the high diffusion rate characteristic of the inside-out configuration.

In accordance with the invention, any small molecule, organic compounds, peptides, toxins, antibodies, or proteins, especially those present in medicinal or agricultural libraries, may used as a test substance and applied to the cell membrane in a patch clamp measurement, for example.

In accordance with the present invention, the apparatuses and methods disclosed herein may be used in screens to identify compounds or processes that affect cellular electrical properties. Non-limiting examples of compounds that can be identified include neurotransmitters, neurotransmitter analogues, enzyme inhibitors, ion channel modulators, G-proteins and their ligands, modulators, and receptors, transport inhibitors, hormones, peptides, toxins, antibodies, pharmaceutical agents, chemicals, and any combination of these compounds.

Specific compounds that are of interest include ion channel modulators (blockers, openers, gating modifiers), purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and any combination of these compounds.

Cellular processes that may be identified by the screens disclosed herein include cell-cell interaction, cell-cell fusion, viral infection, endocytosis, exocytosis, membrane recycling, and membrane-ligand. As all cellular process can cause a measurable change in one or more of the electrical properties of the cell, the present invention can be used to study any such process. In turn, these studies can be used to discover compounds that modulate cellular processes.

An advantage of the invention is that it dispenses with the need for additional tubing or accessories, which significantly cuts down on cost and accidental contamination with residues that might reside inside a perfusion system. Because test compounds can often adhere to tubing used for perfusion systems, such systems can requiring additional cleaning and/or replacing of the tubing. The invention eliminates this problem.

An advantage of the invention is that it enables fast transfer of the membrane from one well to another. The pipette can simply be removed from one well and inserted in another. There is no need for the time-consuming operations of compound dilution and perfusion system adjustment. Importantly, the often slow step of replacing the contents of a bath chamber containing a cell by perfusion is reduced to the time that it takes to move the pipette from one well to the next. Moreover, the invention dispenses with the need for additional tubing or accessories, which significantly cuts down on cost and accidental contamination with residues that might reside inside a perfusion system. Test compounds can often adhere to tubing used for perfusion systems, requiring cleaning or replacing of the tubing. This problem is eliminated by the systems and methods described herein.

It will be understood that the specific embodiments of the invention shown and described herein are exemplary only. Numerous variations, changes, substitutions and equivalents will occur to those skilled in the art without departing from the spirit and scope of the invention. In particular, the terms used in this application should be read broadly in light of similar terms used in the related applications. Accordingly, it is intended that all subject matter described herein and shown in the accompanying drawings be regarded as illustrative only and not in a limiting sense and that the scope of the invention be solely determined by the appended claims.

What is claimed is:

1. A method of conducting high throughput patch clamp measurements comprising:
   placing a plurality of pipettes in a pipette holder located on a moveable platform that comprises at least a first multi-well compound plate and a second multi-well compound plate, each plate comprising a plurality of wells, and said plurality of wells containing one or more test compounds, control substances or washing solutions;
   affixing a cell to each said pipette;
   moving the moveable platform so that the pipette holder is aligned with a pipette fixture to stably attach the pipettes to the pipette fixture;
   thereafter establishing a plurality of patch clamp configurations in each pipette comprising each cell sealed to each pipette;
   relatively moving the moveable platform to align the pipette fixture and the first multi-well compound plate comprising a plurality of wells so that each cell sealed to a pipette is inside one well of the plurality of wells; and measuring at least one electrical property of at least one said cell of said plurality of patch clamp configurations;
   removing the cells from the first multi-well compound plate by relatively moving the pipette fixture the moveable platform; and
   inserting the cells into at least the second multi-well compound plate by relatively moving the pipette fixture and the moveable platform, and measuring at least one electrical property of at least one said cell of said plurality of patch clamp configurations.

2. The method of claim 1, wherein the action of establishing a plurality of patch clamp configurations comprises establishing an inside-out patch clamp configuration.

3. The method of claim 1, wherein the measuring action comprises: measuring the current between a reference electrode and a patch electrode, wherein the reference electrode is adapted to electrically contact a test solution contained in one of the wells, and the patch electrode is adapted to electrically contact a pipette solution contained in at least one pipette of said plurality of patch clamp configurations.

4. The method of claim 1, wherein each said pipette comprises an electrode.

5. The method of claim 1, further comprising:
   placing each said pipette in a pipette holder, said pipette holder coupled to a moveable platform.

6. The method of claim 5, wherein the affixing action comprises:
   moving the platform relative to the pipette fixture;
   attaching each said pipette to the pipette fixture; and
   disengaging each said pipette from the pipette holder.

7. The method of claim 5, wherein the moveable platform holds the plate.

8. The method of claim 5, wherein the moveable platform is configured to hold a fluid wash system that is substantially conical or tubular in shape.

9. The method of claim 8, further comprising:
   relatively moving the pipette fixture and fluid wash system so at least one of the cells is inside the fluid wash system.

10. The method of claim 9, further comprising:
    pumping fluid into the fluid wash system to wash at least one of the cells.

11. The method of claim 1, wherein at least one of the wells contains a test substance.

12. The method of claim 1, wherein at least one of the wells contains a wash solution.

13. The method of claim 6, wherein the plurality of wells comprises a first set of wells and a second set of wells, further comprising:
    removing the cells from the first set of wells by relatively moving the pipette fixture and plate; and
    inserting the cells into the second set of wells in the plate by relatively moving the pipette fixture and plate.

14. The method of claim 13, wherein at least one of the wells of the second set of wells comprise one or more test substances.

15. The method of claim 13, wherein at least one of the wells of the second set of wells comprise one or more wash solutions.

16. The method of claim 13, wherein at least one of the wells of the first set of wells comprises one or more test substances, and wherein at least one of the wells of the second set of wells comprises at least one of:
    one or more different test substances, or
    the same test substances in different concentrations.

17. The method of claim 13, wherein the plurality of wells further comprises a third set of wells, further comprising:
    removing the cells from the second set of wells by relatively moving the pipette fixture and plate; and
    inserting each said cell into the third set of wells by relatively moving the pipette fixture and plate.

18. The method of claim 17, wherein the second set of wells are different from the third set of wells.

19. The method of claim 1, further comprising:
    removing the cells from the first set of wells by relatively moving the platform and the pipette fixture; and
    inserting the cells into a fluid wash system by relatively moving the pipette fixture and the fluid wash system.

20. The method of claim 1, wherein the establishing action comprises establishing a high resistance electrical seal between each of the cells and each said pipette.

21. The method of claim 20, further comprising: determining whether a high resistance electrical seal has been formed between at least one of the cells and at least one pipette.

22. The method of claim 1, further comprising: exposing each of the cells to ambient air.

23. The method of claim 1, further comprising processing electrical measurement data based on the measuring action.

24. The method of claim 1, wherein said establishing action comprises: applying air pressure inside at least one pipette to move at least one of cell from an interior position inside the pipette to the tip of the pipette.

* * * * *